United States Patent
Liu et al.

(10) Patent No.: US 9,492,118 B1
(45) Date of Patent: Nov. 15, 2016

(54) PRE-TREATMENT PROCESS FOR ELECTROCHEMICAL AMPEROMETRIC SENSOR

(71) Applicant: Verily Life Sciences LLC, Mountain View, CA (US)

(72) Inventors: Zenghe Liu, Alameda, CA (US); Nathan Pletcher, Mountain View, CA (US)

(73) Assignee: Life Sciences LLC, Mountain View, CA (US)

( * ) Notice: Subject to any disclaimer, the term of this patent is extended or adjusted under 35 U.S.C. 154(b) by 523 days.

(21) Appl. No.: 13/930,861

(22) Filed: Jun. 28, 2013

(51) Int. Cl.
| | |
|---|---|
| A61B 5/05 | (2006.01) |
| A61B 5/00 | (2006.01) |
| A61B 5/145 | (2006.01) |
| A61B 5/1468 | (2006.01) |

(52) U.S. Cl.
CPC ........... *A61B 5/6821* (2013.01); *A61B 5/1468* (2013.01); *A61B 5/14532* (2013.01)

(58) Field of Classification Search
CPC ................................................ A61B 5/14532
See application file for complete search history.

(56) References Cited

U.S. PATENT DOCUMENTS

| | | | |
|---|---|---|---|
| 3,958,560 A | 5/1976 | March | |
| 4,014,321 A | 3/1977 | March | |
| 4,055,378 A | 10/1977 | Feneberg et al. | |
| 4,122,942 A | 10/1978 | Wolfson | |
| 4,136,250 A | 1/1979 | Mueller et al. | |
| 4,143,949 A | 3/1979 | Chen | |
| 4,153,641 A | 5/1979 | Deichert et al. | |
| 4,214,014 A | 7/1980 | Hofer et al. | |
| 4,309,085 A | 1/1982 | Morrison | |
| 4,312,575 A | 1/1982 | Peyman et al. | |
| 4,401,371 A | 8/1983 | Neefe | |
| 4,463,149 A | 7/1984 | Ellis | |

(Continued)

FOREIGN PATENT DOCUMENTS

| | | |
|---|---|---|
| EP | 0369942 | 5/1990 |
| EP | 0686372 | 12/1995 |

(Continued)

OTHER PUBLICATIONS

Bionic contact lens 'to project emails before eyes,' http://www.kurzweilai.netforums/topic/bionic-contact-lens-to-project-emails-before-eyes, Last accessed Mar. 14, 2012, 2 pages.

(Continued)

*Primary Examiner* — Christian Jang
(74) *Attorney, Agent, or Firm* — McDonnell, Boehnen, Hulbert & Berghoff LLP

(57) ABSTRACT

A wearable device is provided herein and includes an electrochemical sensor with a working electrode, a reference electrode, and a reagent that selectively reacts with an analyte. In accordance with one embodiment, a process is provided herein and includes applying an electric potential waveform pattern between the working electrode and the reference electrode, the pattern comprising a combination of a constant voltage and at least one voltage waveform including one or more of a triangle waveform, a pulse-step waveform, and a sine waveform, determining a current at the working electrode, the current resulting from the application of the electric potential waveform pattern, determining that the current is less than a threshold level of measured current, and in response, the wearable device stopping the application of the electric potential waveform pattern.

8 Claims, 17 Drawing Sheets

(56) References Cited

U.S. PATENT DOCUMENTS

| | | |
|---|---|---|
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint, Jr. et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,773,429 B2 * | 8/2004 | Sheppard, Jr. ........ A61K 9/0009 600/345 |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,045,054 B1 * | 5/2006 | Buck ................ A61B 5/14532 204/403.1 |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,160,834 B2 | 4/2012 | Liang |
| 8,224,415 B2 | 7/2012 | Budiman |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0101498 A1 | 4/2009 | Papadimitrakopoulos |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder et al. |
| 2012/0109296 A1 | 5/2012 | Fan |

(56) References Cited

U.S. PATENT DOCUMENTS

| | | |
|---|---|---|
| 2012/0177576 A1 | 7/2012 | Hu |
| 2012/0201755 A1 | 8/2012 | Rozakis et al. |
| 2012/0245444 A1 | 9/2012 | Otis et al. |
| 2012/0259188 A1 | 10/2012 | Besling |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Brahim, et al., "Polypyrrole-hydrogel composites for the construction of clinically important biosensors," 2002, Biosensors & Bioelectronics, pp. 53-59, vol. 17.
Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.
Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.
"Contact Lenses: Look Into My Eyes," The Economist, Jun. 2, 2011, http://www.economist.com/node/18750624/print, Last accessed Mar. 13, 2012, 8 pages.
Haders, "New Controlled Release Technologies Broaden Opportunities for Ophthalmic Therapies," Drug Delivery Technology, Jul./Aug. 2009, pp. 48-53, vol. 8, No. 7.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.
Huang, et al., "Wrinkling of Ultrathin Polymer Films," Mater. Res. Soc. Symp. Proc., 2006, 6 pages, vol. 924, Materials Research Society.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Liao, et al., "A 3-µW CMOS Glucose Sensor for Wireless Contact-Lens Tear Glucose Monitoring ," IEEE Journal of Solid-State Circuits, Jan. 2012, pp. 335-344, vol. 47, No. 1.
Liao, et al., "A 3-µW Wirelessly Powered CMOS Glucose Sensor for an Active Contact Lens," 2011 IEEE International Solid-State Circuits Conference, Session 2, Feb. 21, 2011, 3 pages.

Lingley, et al., "A Single-Pixel Wireless Contact Lens Display," Journal of Micromechanics and Microengineering, 2011, pp. 1-8.
Lingley, et al., "Multipurpose integrated active contact lenses," SPIE, 2009, 2 pages.
Liu, et al., "Miniature Amperometric Self-Powered Continuous Glucose Sensor with Linear Response," Analytical Chemistry, 2012, 7 pages.
Loncar, et al., "Design and Fabrication of Silicon Photonic Crystal Optical Waveguides," Journal of Lightwave Technology, Oct. 2000, pp. 1402-1411, vol. 18, No. 10.
Murdan, "Electro-responsive drug delivery from hydrogels," Journal of Controlled Release, 2003, pp. 1-17, vol. 92.
Pandey, et al., "A Fully Integrated RF-Powered Contact Lens With a Single Element Display," IEEE Transactions on Biomedical Circuits and Systems, Dec. 2010, pp. 454-461, vol. 4, No. 6.
Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.
Selner, et al., "Novel Contact Lens Electrode Array for Multi-electrode Electroretinography (meERG)," IEEE, 2011, 2 pages.
Singh, et al., "Novel Approaches in Formulation and Drug Delivery using Contact Lenses," Journal of Basic and Clinical Pharmacy, May 2011, pp. 87-101, vol. 2, Issue 2.
Thomas, et al., "Functional Contact Lenses for Remote Health Monitoring in Developing Countries," IEEE Global Humanitarian Technology Conference, 2011, pp. 212-217, IEEE Computer Society.
Tweedie, et al., "Contact creep compliance of viscoelastic materials via nanoindentation," J. Mater. Res., Jun. 2006, pp. 1576-1589, vol. 21, No. 2, Materials Research Society.
Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.
Zarbin, et al., "Nanotechnology in ophthalmology," Can J Ophthalmol, 2010, pp. 457-476, vol. 45, No. 5.
Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.
Chu et al., "Biomedical soft contact-lens sensor for in situ ocular biomonitoring of tear contents," Biomed Microdevices, 2011, pp. 603-611, vol. 13.
Chu et al., "Soft contact lens biosensor for in situ monitoring of tear glucose as non-invasive blood sugar assessment," Talanta, 2011, pp. 960-965, vol. 83.
Ho et al., "Contact Lens With Integrated Inorganic Semiconductor Devices," MEMS 2008. IEEE 21st International Conference on. IEEE, 2008., pp. 403-406.
Lähdesmaki et al., "Possibilities for Continuous Glucose Monitoring by a Functional Contact Lens," IEEE Instrumentation & Measurement Magazine, Jun. 2010, pp. 14-17.
Lingley et al., "A contact lens with integrated micro solar cells," Microsyst Technol, 2012, pp. 453-458, vol. 18.
Parviz, Babak A., "For Your Eyes Only," IEEE Spectrum, Sep. 2009, pp. 36-41.
Saeedi, E. et al., "Self-assembled crystalline semiconductor optoelectronics on glass and plastic," J. Micromech. Microeng., 2008, pp. 1-7, vol. 18.
Saeedi et al., "Self-Assembled Inorganic Micro-Display on Plastic," Micro Electro Mechanical Systems, 2007. MEMS. IEEE 20th International Conference on. IEEE, 2007., pp. 755-758.
Sensimed Triggerfish, Sensimed Brochure, 2010, 10 pages.
Shih, Yi-Chun et al., "An Inductorless DC-DC Converter for Energy Harvesting With a 1.2-µW Bandgap-Referenced Output Controller," IEEE Transactions on Circuits and Systems-II: Express Briefs, Dec. 2011, pp. 832-836, vol. 58, No. 12.
Shum et al., "Functional modular contact lens," Proc. of SPIE, 2009, pp. 73970K-1 to 73970K-8, vol. 7397.

(56) References Cited

OTHER PUBLICATIONS

Stauth et al., "Self-assembled single-crystal silicon circuits on plastic," PNAS, Sep. 19, 2006, pp. 13922-13927, vol. 103, No. 38.
Yao, H. et al., "A contact lens with integrated telecommunication circuit and sensors for wireless and continuous tear glucose monitoring," J. Micromech. Microeng., 2012, pp. 1-10, vol. 22.
Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.
Yao et al., "A contact lens with embedded sensor for monitoring tear glucose level," Biosensors and Bioelectronics, 2011, pp. 3290-3296, vol. 26.
Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.
Yeager et al., "A 9 µA, Addressable Gent Sensor Tag for Biosignal Acquistion," IEEE Journal of Solid-State Circuits, Oct. 2010, pp. 2198-2209, vol. 45, No. 10.
Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.
Pending U.S. Appl. No. 13/650,248, titled "In-vitro Calibration of an Ophthalmic Analyte Sensor," first named inventor: Liu.

* cited by examiner

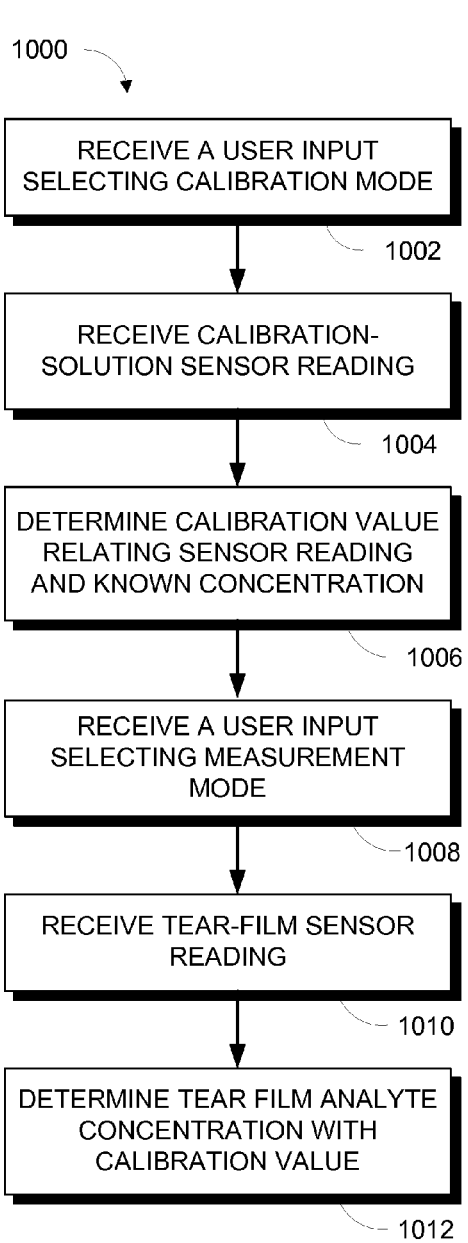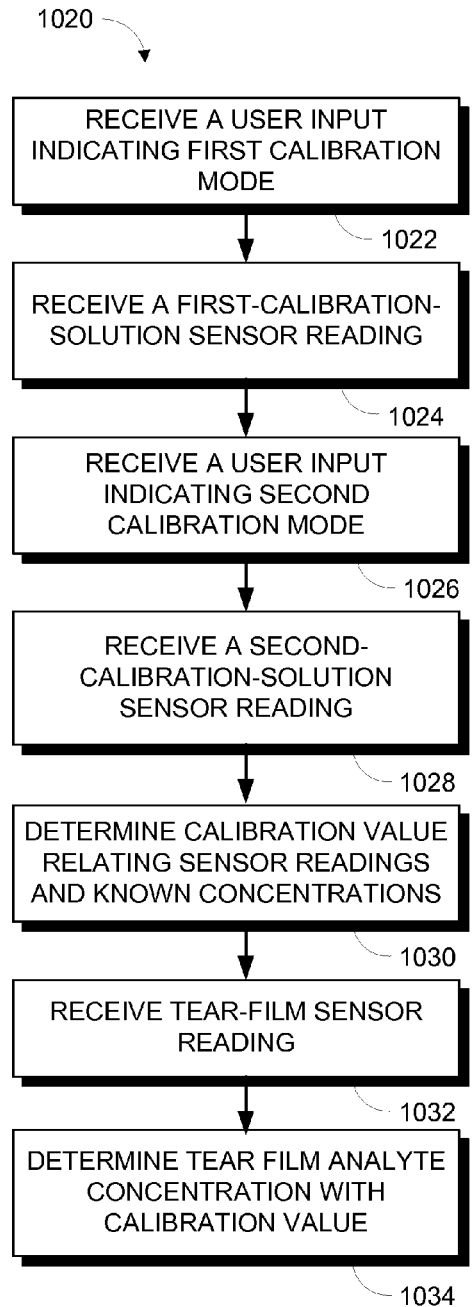
FIG. 10A　　　　FIG. 10B

PRE-TREATMENT PROCESS FOR ELECTROCHEMICAL AMPEROMETRIC SENSOR

BACKGROUND

Unless otherwise indicated herein, the materials described in this section are not prior art to the claims in this application and are not admitted to be prior art by inclusion in this section.

An electrochemical amperometric sensor measures a concentration of an analyte by measuring a current generated through electrochemical oxidation or reduction reactions of the analyte at a working electrode of the sensor. A reduction reaction occurs when electrons are transferred from the electrode to the analyte, whereas an oxidation reaction occurs when electrons are transferred from the analyte to the electrode. The direction of the electron transfer is dependent upon the electrical potentials applied to the working electrode by a potentiostat. A counter electrode and/or reference electrode is used to complete a circuit with the working electrode and allow the generated current to flow. When the working electrode is appropriately biased, the output current is proportional to the reaction rate, which provides a measure of the concentration of the analyte surrounding the working electrode. Ideally, the output current is linearly related to the actual concentration of the analyte, and the linear relationship can therefore be characterized by a two parameter fit (e.g., slope and intercept).

In some examples, a reagent is localized proximate the working electrode to selectively react with a desired analyte. For example, glucose oxidase can be fixed near the working electrode to react with glucose and release hydrogen peroxide, which is then electrochemically detected by the working electrode to indicate the presence of glucose. Other enzymes and/or reagents can be used to detect other analytes.

SUMMARY

Some embodiments of the present disclosure provide a method including a wearable device applying an electric potential waveform pattern between a working electrode and a reference electrode. The wearable device may include an electrochemical sensor with a working electrode, a reference electrode, and a reagent that selectively reacts with an analyte. The pattern may include a combination of a constant voltage and at least one voltage waveform including one or more of a triangle waveform, a pulse-step waveform, and a sine waveform. The method may further include determining a current at the working electrode, the current resulting from the application of the electric potential waveform pattern, determining that the current is less than a threshold level of measured current, and in response, the wearable device stopping the application of the electric potential waveform pattern.

Some embodiments of the present disclosure provide a system including an eye-mountable device and a reader. The wearable device may include an antenna, an electrochemical sensor that includes a working electrode, a reference electrode, and a reagent that selectively reacts with an analyte, and a controller electrically connected to the electrochemical sensor and the antenna. The controller may be configured to control the electrochemical sensor to obtain a sensor measurement while the wearable device is exposed to a fluid, and use the antenna to transmit the sensor measurement. The reader may be operable in a pre-treatment mode and a measurement mode. In the pre-treatment mode, the reader may be configured to (i) wirelessly communicate with the antenna to cause the controller to apply an electric potential waveform pattern between the working electrode and the reference electrode of the electrochemical sensor, the pattern comprising a combination of a constant voltage and at least one voltage waveform including one or more of a triangle waveform, a pulse-step waveform, and a sine waveform, (ii) wirelessly communicate with the antenna to receive a pre-treatment measurement obtained while the wearable device is exposed to a buffer solution substantially devoid of the analyte, (iii) determine that the pre-treatment measurement is less than a threshold level, and (iv) in response to the determination, wirelessly communicate with the antenna to cause the wearable device to stop applying the electric potential waveform pattern. In the measurement mode, the reader may be configured to wirelessly communicate with the antenna to receive a tear-film sensor measurement obtained with the wearable device exposed to a tear film and determine a concentration of the analyte in the tear film based on the tear-film sensor measurement.

Some embodiments of the present disclosure provide a non-transitory computer readable medium storing instructions that, when executed by one or more processors in a computing device, cause the computing device to perform operations. The operations can include applying an electric potential waveform pattern between a working electrode and a reference electrode. The pattern may include a combination of a constant voltage and at least one voltage waveform including one or more of a triangle waveform, a pulse-step waveform, and a sine waveform, the electric potential waveform pattern being applied based on the wearable device being exposed to a buffer solution that is substantially devoid of the analyte. The operations may also include determining a current at the working electrode, the current resulting from the application of the electric potential waveform pattern, determining that the measured current is less than a threshold level of measured current, and in response, the wearable device stopping the application of the electric potential waveform pattern.

These as well as other aspects, advantages, and alternatives, will become apparent to those of ordinary skill in the art by reading the following detailed description, with reference where appropriate to the accompanying figures.

BRIEF DESCRIPTION OF THE FIGURES

FIG. 10A is a flowchart of an example calibration process that uses a single calibration data point, in accordance with one embodiment.

FIG. 10B is a flowchart of an example calibration process that uses multiple calibration data points, in accordance with one embodiment.

DETAILED DESCRIPTION

Figure 1:
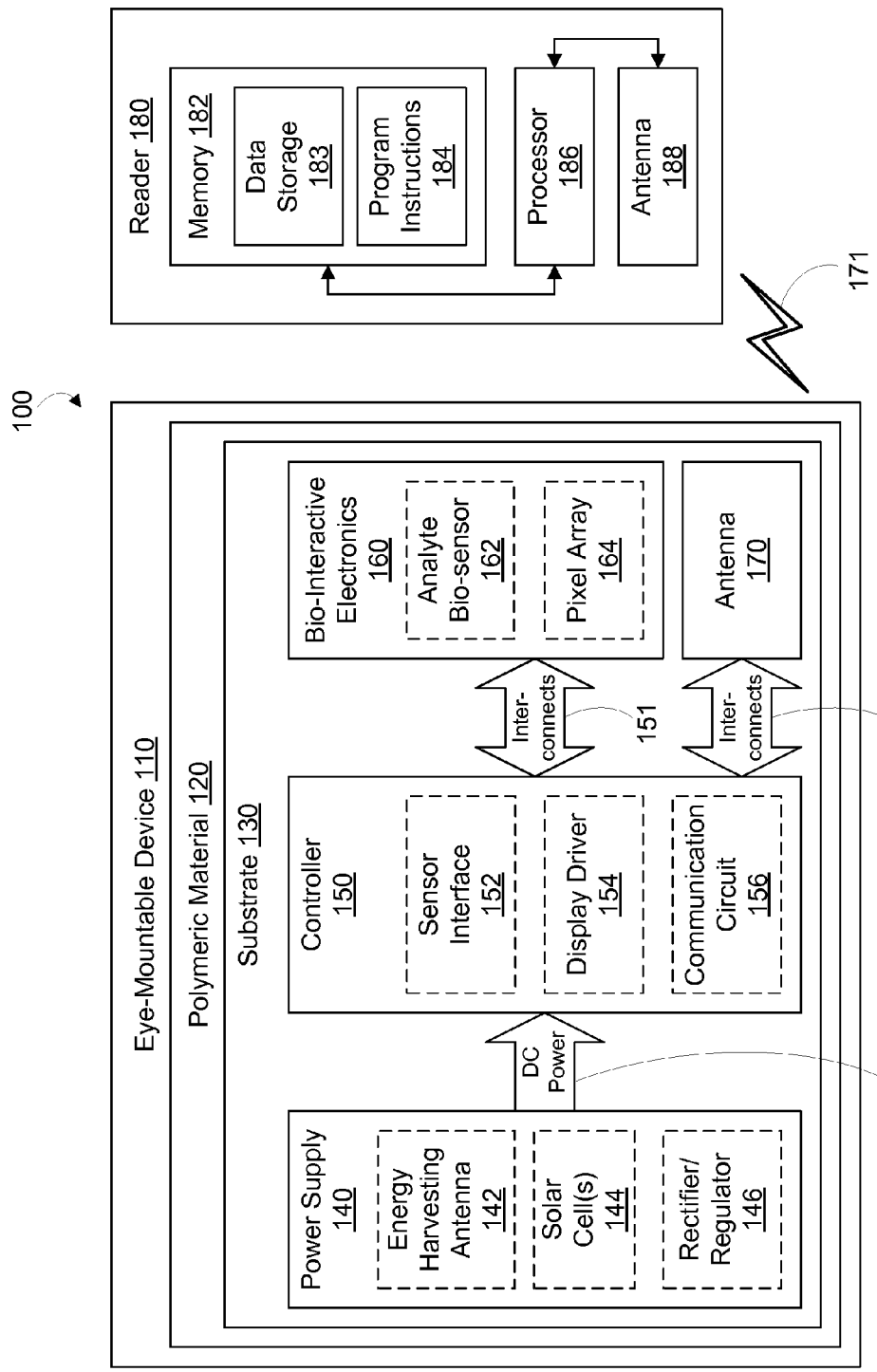
FIG. 1 is a block diagram of an example system that includes an eye-mountable device in wireless communication with an external reader, in accordance with one embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

An ophthalmic sensing platform can include a sensor, control electronics and an antenna all situated on a substrate embedded in a polymeric material formed to be contact mounted to an eye. The control electronics can operate the sensor to perform readings and can operate the antenna to wirelessly communicate the readings from the sensor to an external reader via the antenna.

The polymeric material can be in the form of a round lens with a concave curvature configured to mount to a corneal surface of an eye. The substrate can be embedded near the periphery of the polymeric material to avoid interference with incident light received closer to the central region of the cornea. The sensor can be arranged on the substrate to face inward, toward the corneal surface, so as to generate clinically relevant readings from near the surface of the cornea and/or from tear fluid interposed between the contact lens and the corneal surface. In some examples, the sensor is entirely embedded within the contact lens material. For example, an electrochemical sensor that includes a working electrode can be suspended in the lens material and situated such that the working electrode is less than about 10 micrometers from the polymeric surface configured to mount to the cornea. The sensor can generate an output signal indicative of a concentration of an analyte that diffuses through the lens material to the embedded sensor.

The ophthalmic sensing platform can be powered via radiated energy harvested at the sensing platform. Power can be provided by light energizing photovoltaic cells included on the sensing platform. Additionally or alternatively, power can be provided by radio frequency energy harvested from the antenna. A rectifier and/or regulator can be incorporated with the control electronics to generate a stable DC voltage to power the sensing platform from the harvested energy. The antenna can be arranged as a loop of conductive material with leads connected to the control electronics. In some embodiments, such a loop antenna can wirelessly also communicate the sensor readings to an external reader by modifying the impedance of the loop antenna so as to modify backscatter radiation from the antenna.

Tear fluid contains a variety of inorganic electrolytes (e.g., $Ca^{2+}$, $Mg^{2+}$, $Cl^-$), organic components (e.g., glucose, lactate, proteins, lipids, etc.), and so on that can be used to diagnose health states. The ophthalmic sensing platform can measure one or more of these components and provide a convenient non-invasive platform to diagnose or monitor health related problems. For example, the ophthalmic sensing platform can be configured to sense glucose and be used to measure glucose levels in diabetic patients.

Manufacturing variations in electrode geometry, smoothness, impurities, sensing reagent deposition, polymeric membrane thickness, or other types of electrode variations can cause differences in sensor sensitivities. As a result, different sensors may produce inconsistent measurement results. For example, sensors that have a linear relationship relating measured current to analyte concentration that also have different sensitivities will produce measurements that vary in terms of intercept and/or slope. Moreover, degradation of the electrochemical sensor itself, such as chemical change of the electrode surfaces, denaturation of the sensing reagent, or other electrode changes can also cause the sensitivity and/or intercept of the sensor to change over time.

The present disclosure provides a technique for engaging in a pre-treatment process to address possible sensor variations. In accordance with one example pre-treatment process, before the sensor is used in a measurement process it is exposed to a buffer solution, such as blank phosphate buffered saline (PBS). While exposed, an electrical potential pattern is applied to the sensor. This application of electrical potential to the sensor in the presence of the blank buffer solution may cause microscopic gas bubbles to form in the buffer solution that effectively clean the surface of the sensor's electrode. During the application of the electrical potential, an electric current flows in the working electrode. This current generally decreases over the course of the application. The pattern is applied continuously until sensor current decreases to a threshold level of current or is sufficiently stable for a threshold period of time.

The present disclosure also provides a technique for calibrating readings from the ophthalmic sensing platform. In accordance with one example calibration, upon completion of a pre-treatment process, the sensor is exposed to a calibration solution with a known concentration of the analyte of interest. The calibration solution could be, for example, an artificial solution with a composition that is similar to that of a normal tear film. While exposed, a sensor reading is obtained. This technique can be employed to calibrate an ophthalmic sensing platform even though the volume of sampled tear film may be very limited. In contrast to calibration techniques that calibrate sensor readings using a measurement of the same sample fluid with a second reliable sensor and/or method, the present disclosure allows for calibration using a reading with the same sensor while sampling a calibrated solution. The present disclosure thereby allows for calibrating sensor readings without obtaining a second sample fluid.

The ophthalmic sensing platform can be exposed to a calibration solution with known analyte concentration and a sensor reading is obtained while the ophthalmic sensing platform remains exposed. The sensor result (e.g., the amperometric current) divided by the concentration of the analyte can be set as the sensitivity of the ophthalmic sensing platform, and a linear relationship can be established with the sensitivity as the slope to relate future and/or past sensor results to analyte concentrations.

The ophthalmic sensing platform can be submerged to soak in the calibration solution. Where the ophthalmic sensing platform is stored dry, the ophthalmic sensing platform is transferred into the solution to expose the ophthalmic sensing platform to the known analyte concentration of the calibration solution. Where the ophthalmic sensing platform is stored in a soaking solution, the calibration solution can be created by adding a known volume of calibration solution to the soaking solution. For example, adding a volume of the calibration solution equal to the volume of the soaking solution creates a solution with an analyte concentration one-half of the concentration of the added calibration solution. The base compositions of the calibration solution and/or soaking solution can optionally be similar to the composition of normal tear fluid.

In some examples, the calibration process is initiated by signaling the external reader to indicate the ophthalmic sensing platform is exposed to the calibration solution with known analyte concentration. Such a signal can be generated by, for example, a user input. The external reader can emit radio frequency radiation to be harvested by the ophthalmic sensing platform to power the sensor and control electronics to perform a sensor reading and communicate the result back to the reader. The external reader can extract from the reading, a calibration value relating the sensor readings to analyte concentrations. That is, the calibration value can be a slope and/or intercept characterizing a linear relationship relating amperometric currents measured with the electrochemical sensor and analyte concentrations. Subsequent sensor readings can then be interpreted according to the calibrated relationship set by the sensor readings obtained with the calibration solution.

In some examples, the calibration process includes measuring two or more calibration solutions with known concentrations to perform a calibration. Thus, the sensor reading can be obtained while exposed to a second calibration solution with a second analyte concentration. Additionally or alternatively, the sensor output can be recorded while exposed to a solution with an analyte concentration of zero to provide a zero concentration sensor reading, which can be used to identify, for example, an intercept in a linear relationship relating the sensor readings and analyte concentration levels.

II. Example Ophthalmic Electronics Platform

FIG. 1 is a block diagram of a system 100 that includes an eye-mountable device 110 in wireless communication with an external reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature.

While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some instances, the polymeric material 120 can be a deformable ("non-rigid") material to enhance wearer comfort. In some instances, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc. to create electrodes, interconnects, antennae, etc. In some embodiments, substantially transparent conductive materials (e.g., indium tin oxide) can be patterned on the substrate 130 to form circuitry, electrodes, etc. For example, the antenna 170 can be formed by depositing a pattern of gold or another conductive material on the substrate 130. Similarly, interconnects 151, 157 between the controller 150 and the bio-interactive electronics 160, and between the controller 150 and the antenna 170, respectively, can be formed by depositing suitable patterns of conductive materials on the substrate 130. A combination of resists, masks, and deposition techniques can be employed to pattern materials on the substrate 130. The substrate 130 can be a relatively rigid material, such as polyethylene terephthalate ("PET") or another material sufficient to structurally support the circuitry and/or electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the eye through the center of the eye-mountable device 110. For example, where the eye-mountable device 110 is shaped as a concave-curved disk, the substrate 130 can be embedded around the periphery (e.g., near the outer circumference) of the disk. In some embodiments, the bio-interactive electronics 160 (and the substrate 130) can be positioned in the center region of the eye-mountable device 110. The bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be perceived by the eye according to display instructions. Thus, the bio-interactive electronics 160 can optionally be positioned in the center of the eye-mountable device so as to generate perceivable visual cues to a wearer of the eye-mountable device 110, such as by displaying information via the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the external reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such an analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent can also be included to sensitize the electrochemical sensor to one or more desired analytes. For example, a layer of glucose oxidase ("GOD") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

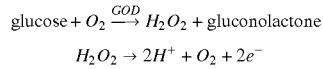

$$glucose + O_2 \xrightarrow{GOD} H_2O_2 + gluconolactone$$

$$H_2O_2 \rightarrow 2H^+ + O_2 + 2e^-$$

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, micro-electromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivably by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The external reader 180 includes an antenna 188 (or group of more than one antennae) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g. RAM)

or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the eye-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earing, etc. or integrated in an article of clothing worn near the head, such as a hat, headband, etc.

In an example in which the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the external reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the external reader 180 (e.g., via the communication circuit 156). The sensor reading can be communicated by, for example, modulating an impedance of the communication antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

Further, some embodiments of the system may include privacy controls which may be automatically implemented or controlled by the wearer of the device. For example, in embodiments in which a wearer's collected physiological parameter data and health state data are uploaded to a cloud computing network for trend analysis by a clinician, the data may be treated in one or more ways before it is stored or used, so that personally identifiable information is removed. For example, a wearer's identity may be treated so that no personally identifiable information can be determined for the wearer, or a wearer's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a wearer's preferences, or a wearer's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 2A:
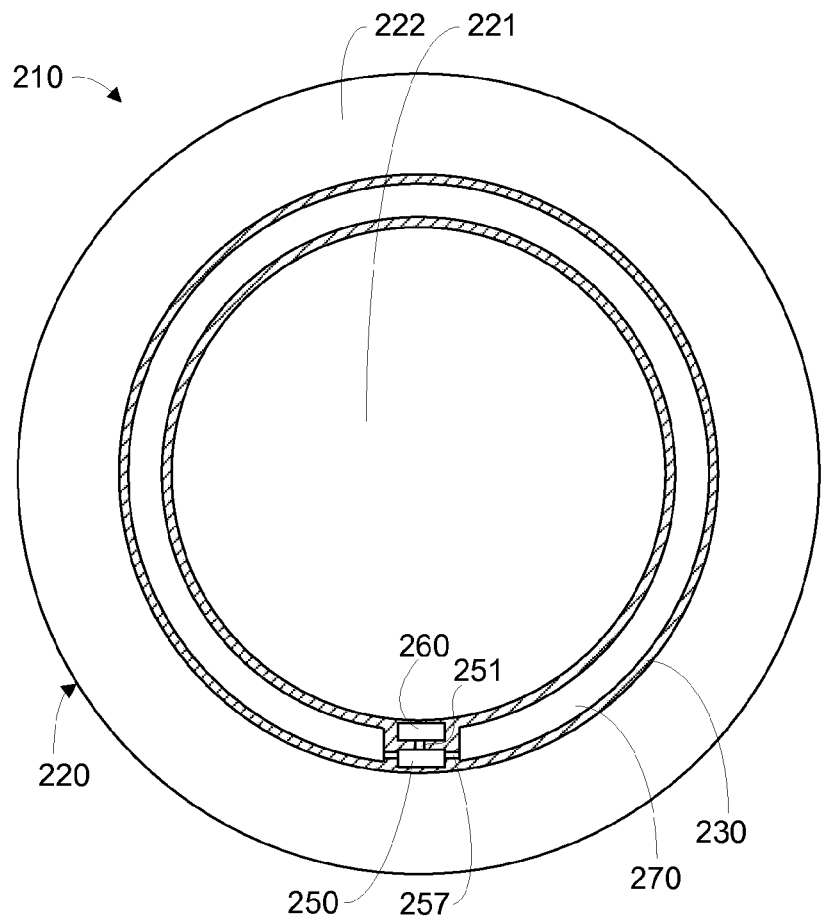
FIG. 2A is a bottom view of an example eye-mountable device, in accordance with one embodiment.
Figure 2B:
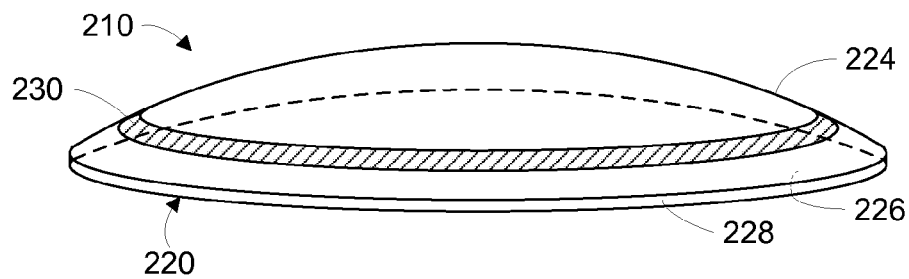
FIG. 2B is an aspect view of the example eye-mountable device shown in FIG. 2A, in accordance with one embodiment.

FIG. 2A is a bottom view of an example eye-mountable electronic device 210. FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, combinations of these, etc. The polymeric material 220 can be formed with one side having a concave surface 226 suitable to fit over a corneal surface of an eye. The opposing side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved out of the page, whereas the center region 221, near the center of the disk is curved in to the page.

A substrate 230 is embedded in the polymeric material 220. The substrate 230 can be embedded to be situated along the outer periphery 222 of the polymeric material 220, away from the center region 221. The substrate 230 does not interfere with vision because it is too close to the eye to be in focus and is positioned away from the center region 221 where incident light is transmitted to the eye-sensing portions of the eye. Moreover, the substrate 230 can be formed of a transparent material to further mitigate any effects on visual perception.

The substrate 230 can be shaped as a flat, circular ring (e.g., a disk with a central hole). The flat surface of the substrate 230 (e.g., along the radial width) is a platform for mounting electronics such as chips (e.g., via flip-chip mounting) and for patterning conductive materials (e.g., via deposition techniques) to form electrodes, antenna(e), and/or connections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors.

A loop antenna 270, controller 250, and bio-interactive electronics 260 are disposed on the embedded substrate 230. The controller 250 can be a chip including logic elements configured to operate the bio-interactive electronics 260 and the loop antenna 270. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) can be formed from conductive materials patterned on the substrate 230 by a process for precisely patterning such materials, such as deposition, lithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the concave surface 226 of the eye-mountable device 210, the bio-interactive electronics module 260 is mounted to a side of the substrate 230 facing the concave surface 226. Where the bio-interactive electronics module 260 includes an analyte bio-sensor, for example, mounting such a bio-sensor on the substrate 230 to be close to the concave surface 226 allows the bio-sensor to sense analyte concentrations in tear film near the surface of the eye. However, the electronics, electrodes, etc. situated on the substrate 230 can be mounted to either the "inward" facing side (e.g., situated closest to the concave surface 226) or the "outward" facing side (e.g., situated closest to the convex surface 224). Moreover, in some embodiments, some electronic components can be mounted on one side of the substrate 230, while other electronic components are mounted to the opposing side, and connections between the two can be made through conductive materials passing through the substrate 230.

The loop antenna 270 is a layer of conductive material patterned along the flat surface of the substrate to form a flat conductive ring. In some instances, the loop antenna 270 can be formed without making a complete loop. For instance, loop antenna 270 can have a cutout to allow room for the controller 250 and bio-interactive electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-interactive electronics 260. Interconnects between the ends of such a wound antenna (e.g., the antenna leads) can be passed through the substrate 230 to the controller 250.

Figure 2D:
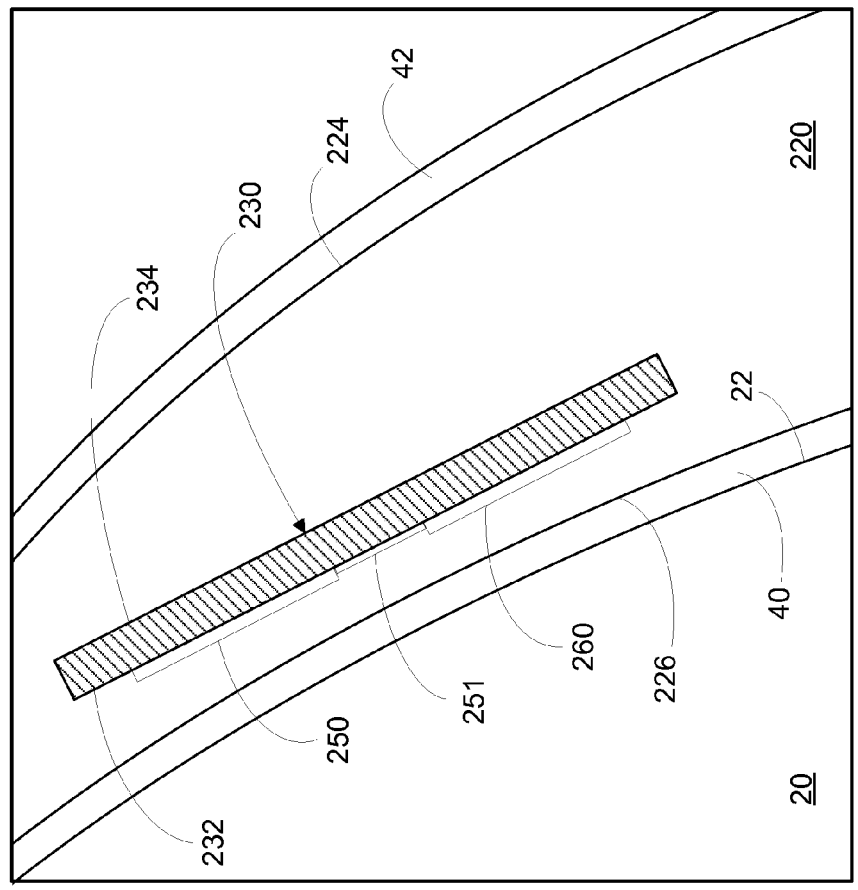
FIG. 2D is a side cross-section view enhanced to show the tear film layers surrounding the surfaces of the example eye-mountable device when mounted as shown in FIG. 2C, in accordance with one embodiment.
Figure 2C:
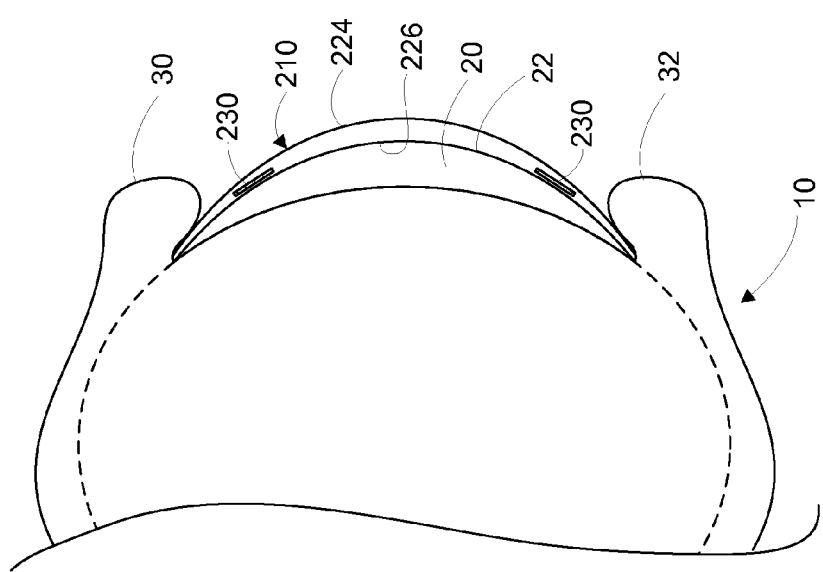
FIG. 2C is a side cross-section view of the example eye-mountable device shown in FIGS. 2A and 2B while mounted to a corneal surface of an eye, in accordance with one embodiment.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the exposed surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 10 micrometers in thickness and together account for about 10 microliters.

The tear film layers 40, 42 are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the concave surface 226. As described above, the substrate 230 is a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the bio-interactive electronics 260, controller 250, and conductive interconnect 251 are mounted on the inward-facing surface 232 such that the bio-interactive electronics 260 are relatively closer in proximity to the corneal surface 22 than if they were mounted on the outward-facing surface 234.

III. Example Ophthalmic Electrochemical Analyte Sensor

Figure 3:
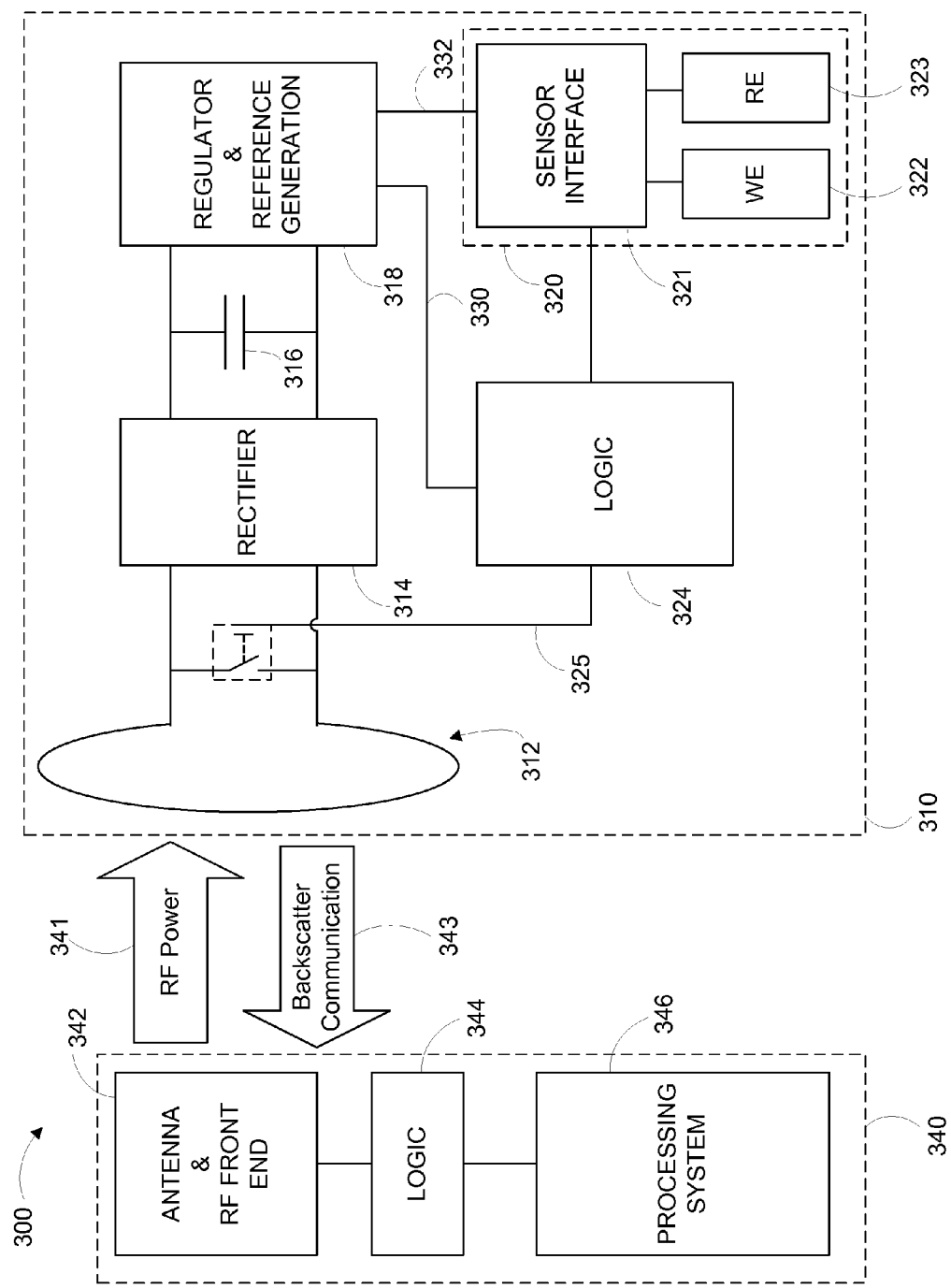
FIG. 3 is a functional block diagram of an example system for electrochemically measuring a tear film analyte concentration, in accordance with one embodiment.

FIG. 3 is a functional block diagram of a system 300 for electrochemically measuring a tear film analyte concentration. The system 300 includes an eye-mountable device 310 with embedded electronic components powered by an external reader 340. The eye-mountable device 310 includes an antenna 312 for capturing radio frequency radiation 341 from the external reader 340. The eye-mountable device 310 includes a rectifier 314, an energy storage 316, and regulator 318 for generating power supply voltages 330, 332 to operate the embedded electronics. The eye-mountable device 310 includes an electrochemical sensor 320 with a working electrode 322 and a reference electrode 323 driven by a sensor interface 321. The eye-mountable device 310 includes hardware logic 324 for communicating results from the sensor 320 to the external reader 340 by modulating (325) the impedance of the antenna 312. Similar to the eye-mountable devices 110, 210 discussed above in connection with FIGS. 1 and 2, the eye-mountable device 310 can include a mounting substrate embedded within a polymeric material configured to be mounted to an eye. The electrochemical sensor 320 can be situated on a mounting surface of such a substrate proximate the surface of the eye (e.g., corresponding to the bio-interactive electronics 260 on the inward-facing side 232 of the substrate 230) to measure analyte concentration in a tear film layer interposed between the eye-mountable device 310 and the eye (e.g., the inner tear film layer 40 between the eye-mountable device 210 and the corneal surface 22). In some embodiments, however, an electrochemical sensor can be situated on a mounting surface of such a substrate distal the surface of the eye (e.g., corresponding to the outward-facing side 234 of the substrate 230) to measure analyte concentration in a tear film layer coating the exposed surface of the eye-mountable device 310 (e.g., the outer tear film layer 42 interposed between the convex surface 224 of the polymeric material 210 and the atmosphere and/or closed eyelids).

With reference to FIG. 3, the electrochemical sensor 320 measures analyte concentration by applying a voltage between the electrodes 322, 323 that is sufficient to cause products of the analyte catalyzed by the reagent to electrochemically react (e.g., a reduction and/or oxidization reaction) at the working electrode 322. The electrochemical reactions at the working electrode 322 generate an amperometric current that can be measured at the working electrode 322. The sensor interface 321 can, for example, apply a reduction voltage between the working electrode 322 and the reference electrode 323 to reduce products from the reagent-catalyzed analyte at the working electrode 322. Additionally or alternatively, the sensor interface 321 can apply an oxidization voltage between the working electrode 322 and the reference electrode 323 to oxidize the products from the reagent-catalyzed analyte at the working electrode 322. The sensor interface 321 measures the amperometric current and provides an output to the hardware logic 324. The sensor interface 321 can include, for example, a potentiostat connected to both electrodes 322, 323 to simultaneously apply a voltage between the working electrode 322 and the reference electrode 323 and measure the resulting amperometric current through the working electrode 322.

The rectifier 314, energy storage 316, and voltage regulator 318 operate to harvest energy from received radio frequency radiation 341. The radio frequency radiation 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter out high frequency components of the DC voltage. The regulator 318 receives the filtered DC voltage and outputs both a digital supply voltage 330 to operate the hardware logic 324 and an analog supply voltage 332 to operate the electrochemical sensor 320. For example, the analog supply voltage can be a voltage used by the sensor interface 321 to apply a voltage between the sensor electrodes 322, 323 to generate an amperometric current. The digital supply voltage 330 can be a voltage suitable for driving digital logic circuitry, such as approximately 1.2 volts, approximately 3 volts, etc. Reception of the radio frequency radiation 341 from the external reader 340 (or another source, such as ambient radiation, etc.) causes the supply voltages 330, 332 to be supplied to the sensor 320 and hardware logic 324. While powered, the sensor 320 and hardware logic 324 are configured to generate and measure an amperometric current and communicate the results.

The sensor results can be communicated back to the external reader 340 via backscatter radiation 343 from the antenna 312. The hardware logic 324 receives the output current from the electrochemical sensor 320 and modulates (325) the impedance of the antenna 312 in accordance with the amperometric current measured by the sensor 320. The antenna impedance and/or change in antenna impedance is detected by the external reader 340 via the backscatter signal 343. The external reader 340 can include an antenna front end 342 and logic components 344 to decode the information indicated by the backscatter signal 343 and provide digital inputs to a processing system 346. The external reader 340 associates the backscatter signal 343 with the sensor result (e.g., via the processing system 346 according to a pre-programmed relationship associating impedance of the antenna 312 with output from the sensor 320). The processing system 346 can then store the indicated sensor results (e.g., tear film analyte concentration values) in a local memory and/or an external memory (e.g., by communicating with the external memory through a network).

In some embodiments, one or more of the features shown as separate functional blocks can be implemented ("packaged") on a single chip. For example, the eye-mountable device 310 can be implemented with the rectifier 314, energy storage 316, voltage regulator 318, sensor interface 321, and the hardware logic 324 packaged together in a single chip or controller module. Such a controller can have interconnects ("leads") connected to the loop antenna 312 and the sensor electrodes 322, 323. Such a controller operates to harvest energy received at the loop antenna 312, apply a voltage between the electrodes 322, 323 sufficient to develop an amperometric current, measure the amperometric current, and indicate the measured current via the antenna 312 (e.g., through the backscatter radiation 343).

Whereas the device described herein is described as comprising the eye-mountable device 110 and/or the eye-mountable device 310, the device could comprise other devices that are mounted on or in other portions of the human body.

For example, in some embodiments, the body-mountable device may comprise a tooth-mountable device. In some embodiments, the tooth-mountable device may take the form of or be similar in form to the eye-mountable device 110 and/or the eye-mountable device 310. For instance, the tooth-mountable device could include a polymeric material or a transparent polymer that is the same or similar to any of the polymeric materials or transparent polymers described herein and a substrate or a structure that is the same or similar to any of the substrates or structures described herein. With such an arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 110 and/or the eye-mountable device 310. For instance, the skin-mountable device could include a polymeric material or a transparent polymer that is the same or similar to any of the polymeric materials or transparent polymers described herein and a substrate or a structure that is the same or similar to any of the substrates or structures described herein. With such an arrangement, the skin-mountable device may be configured to detect at least one analyte in a fluid (e.g., perspiration, blood, etc.) of a user wearing the skin-mountable device.

Figure 4A:
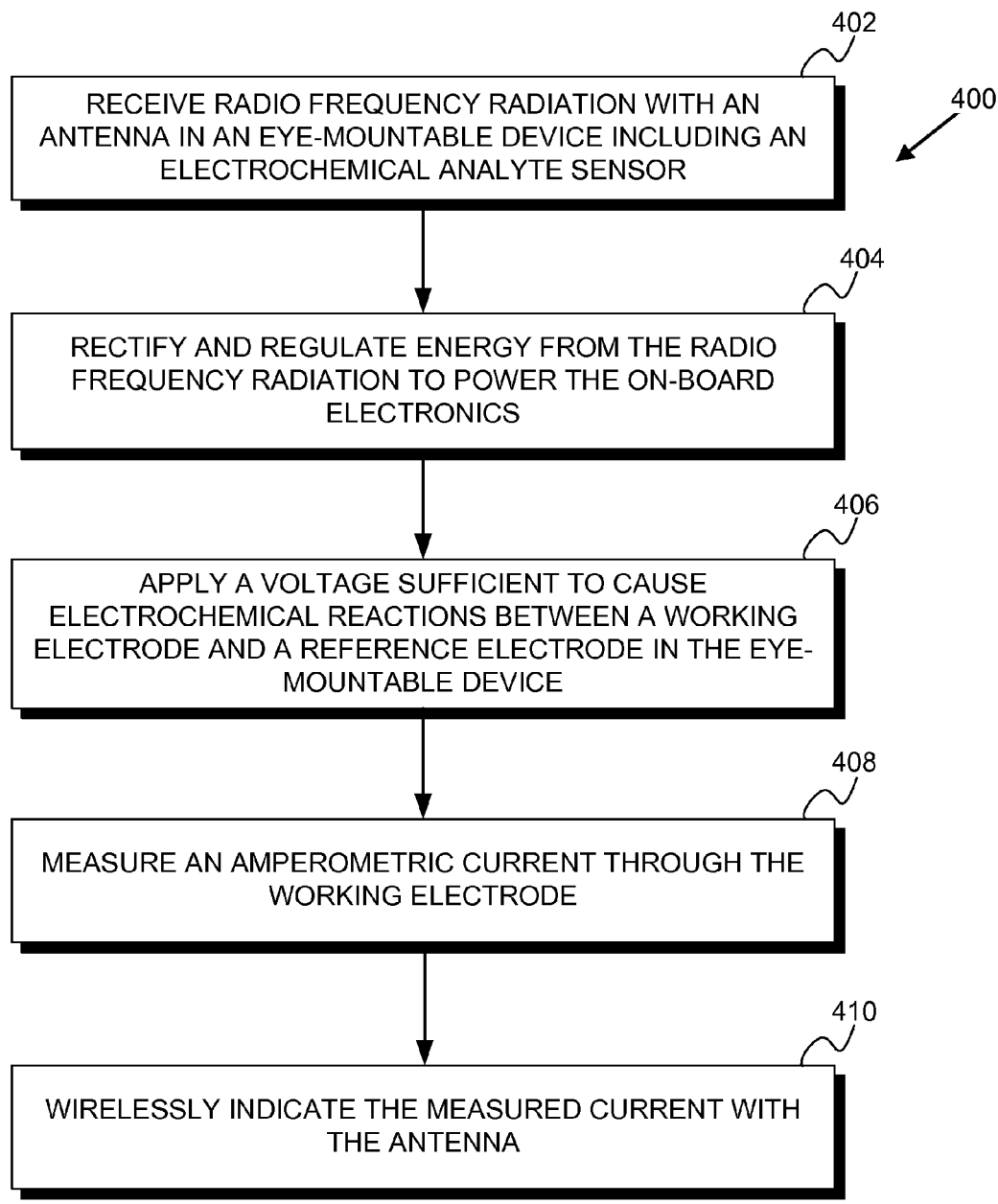
FIG. 4A is a flowchart of an example process for operating an amperometric sensor in an eye-mountable device to measure a tear film analyte concentration, in accordance with one embodiment.

FIG. 4A is a flowchart of a process 400 for operating an amperometric sensor in an eye-mountable device to measure a tear film analyte concentration. Radio frequency radiation is received at an antenna in an eye-mountable device including an embedded electrochemical sensor (402). Electrical signals due to the received radiation are rectified and regulated to power the electrochemical sensor and associated controller (404). For example, a rectifier and/or regulator can be connected to the antenna leads to output a DC supply voltage for powering the electrochemical sensor and/or controller. A voltage sufficient to cause electrochemical reactions at the working electrode is applied between a working electrode and a reference electrode on the electrochemical sensor (406). An amperometric current is measured through the working electrode (408). For example, a potentiostat can apply a voltage between the working and reference electrodes while measuring the resulting amperometric current through the working electrode. The measured amperometric current is wirelessly indicated with the antenna (410). For example, backscatter radiation can be manipulated to indicate the sensor result by modulating the antenna impedance.

Figure 4B:
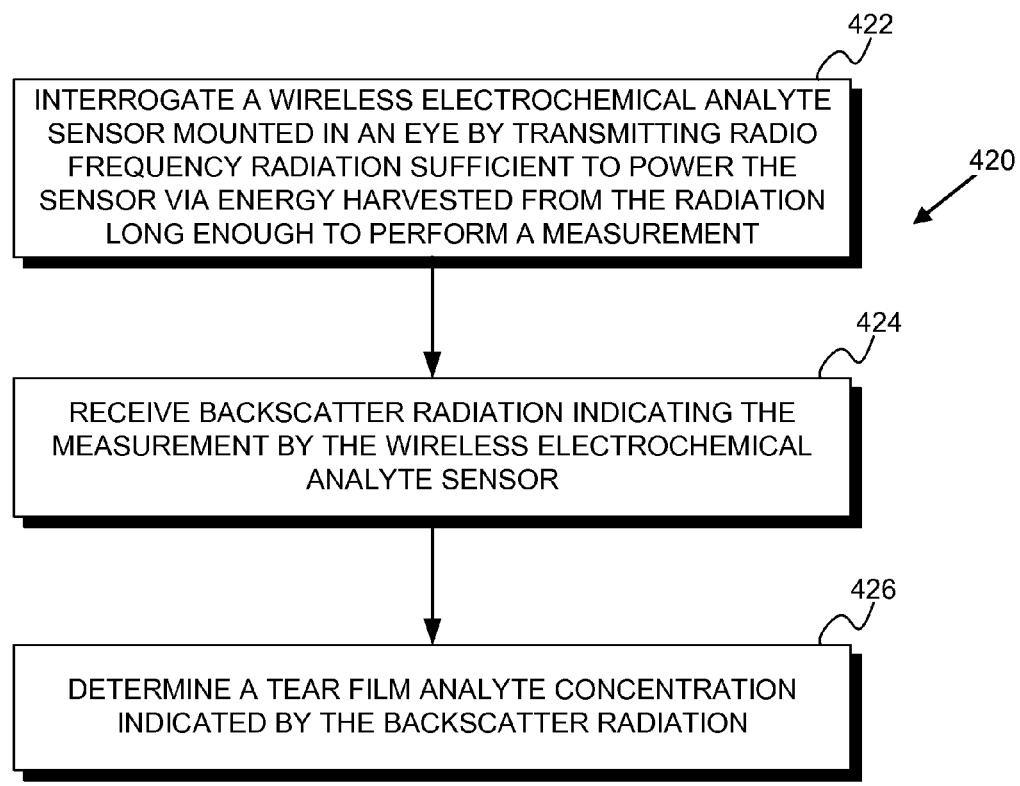
FIG. 4B is a flowchart of an example process for operating an external reader to interrogate an amperometric sensor in an eye-mountable device to measure a tear film analyte concentration, in accordance with one embodiment.

FIG. 4B is a flowchart of a process 420 for operating an external reader to interrogate an amperometric sensor in an eye-mountable device to measure a tear film analyte concentration. Radio frequency radiation is transmitted to an electrochemical sensor mounted in an eye from the external reader (422). The transmitted radiation is sufficient to power the electrochemical sensor with energy from the radiation for long enough to perform a measurement and communicate the results (422). For example, the radio frequency radiation used to power the electrochemical sensor can be similar to the radiation 341 transmitted from the external reader 340 to the eye-mountable device 310 described in connection with FIG. 3 above. The external reader then receives backscatter radiation indicating the measurement by the electrochemical analyte sensor (424). For example, the backscatter radiation can be similar to the backscatter signals 343 sent from the eye-mountable device 310 to the external reader 340 described in connection with FIG. 3 above. The backscatter radiation received at the external reader is then associated with a tear film analyte concentration (426). In some cases, the analyte concentration values can be stored in the external reader memory (e.g., in the processing system 346) and/or a network-connected data storage.

For example, the sensor result (e.g., the measured amperometric current) can be encoded in the backscatter radiation by modulating the impedance of the backscattering antenna. The external reader can detect the antenna impedance and/or change in antenna impedance based on a frequency, amplitude, and/or phase shift in the backscatter radiation. The sensor result can then be extracted by associating the impedance value with the sensor result by reversing the encoding routine employed within the eye-mountable device. Thus, the reader can map a detected antenna impedance value to an amperometric current value. The amperometric current value is approximately proportionate to the tear film analyte concentration with a sensitivity (e.g., scaling factor) relating the amperometric current and the associated tear film analyte concentration. The sensitivity value can be determined in part according to empirically derived calibration factors, for example.

IV. Example Analyte Transmission to the Electrochemical Sensor

Figure 5C:
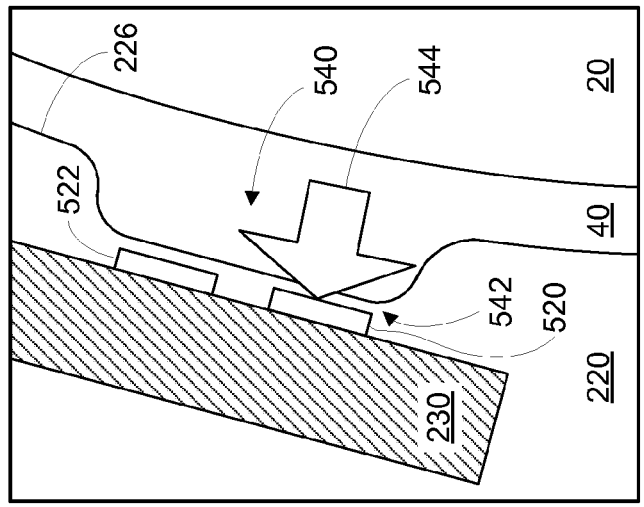
FIG. 5C shows an example configuration in which an electrochemical sensor detects an analyte that diffuses from a tear film through a thinned region of a polymeric material, in accordance with one embodiment.
Figure 5B:
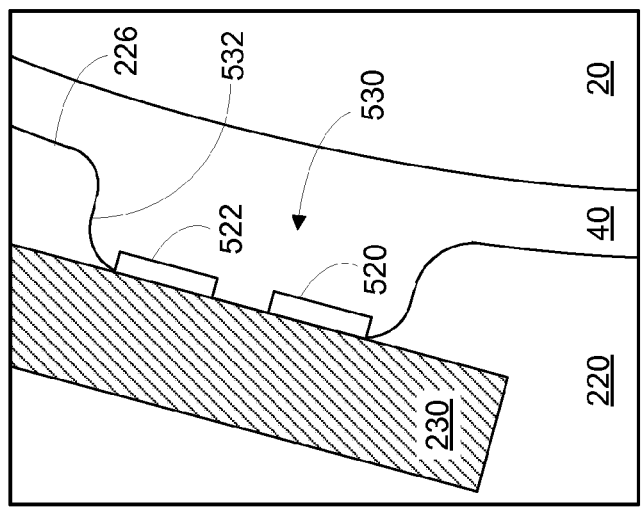
FIG. 5B shows an example configuration in which an electrochemical sensor detects an analyte in a tear film that contacts the sensor via a channel in a polymeric material, in accordance with one embodiment.
Figure 5A:
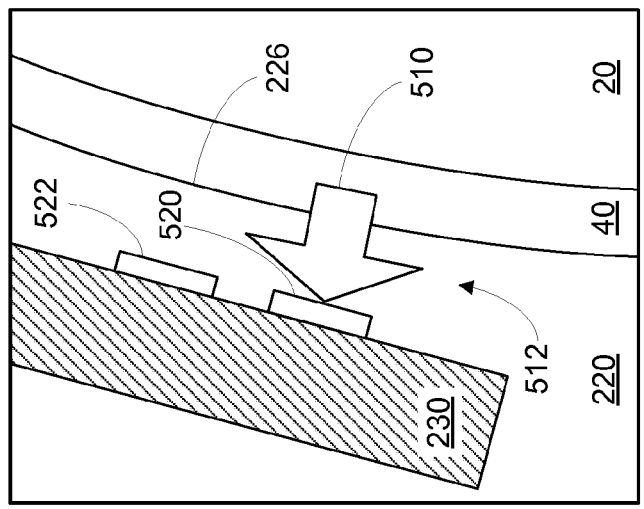
FIG. 5A shows an example configuration in which an electrochemical sensor detects an analyte that diffuses from a tear film through a polymeric material, in accordance with one embodiment.

FIG. 5A shows an example configuration where an electrochemical sensor detects an analyte from the inner tear film layer 40 that diffuses through the polymeric material 220. The electrochemical sensor can be similar to the electrochemical sensor 320 discussed in connection with FIG. 3 and includes a working electrode 520 and a reference electrode 522. The working electrode 520 and the reference electrode 522 are each mounted on an inward-facing side of the substrate 230. The substrate 230 is embedded in the polymeric material 220 of the eye-mountable device 210 such that the electrodes 520, 522 of the electrochemical sensor are entirely covered by an overlapping portion 512 of the polymeric material 220. The electrodes 520, 522 in the electrochemical sensor are thus separated from the inner tear film layer 40 by the thickness of the overlapping portion 512. The thickness of the overlapping region 512 can be approximately 10 micrometers, for example.

An analyte in the tear film diffuses through the overlapping portion 512 to the working electrode 520. The diffusion of the analyte from the inner tear film layer 40 to the working electrode 520 is illustrated by the directional arrow 510. The current measured through the working electrode 520 is based on the electrochemical reaction rate at the working electrode 520, which in turn is based on the amount of analyte diffusing to the working electrode 520. The amount of analyte diffusing to the working electrode 520 can in turn be influenced both by the concentration of analyte in the inner tear film layer 40, the permeability of the polymeric material 220 to the analyte, and the thickness of the overlapping region 512 (i.e., the thickness of polymeric material the analyte diffuses through to reach the working electrode 520 from the inner tear film layer 40). In the steady state approximation, the analyte is resupplied to the inner tear film layer 40 by surrounding regions of the tear film 40 at the same rate that the analyte is consumed at the working electrode 520. Because the rate at which the analyte is resupplied to the probed region of the inner tear film layer 40 is approximately proportionate to the tear film concentration of molecular oxygen, the current (i.e., the electrochemical reaction rate) is an indication of the concentration of the analyte in the inner tear film layer 40.

Where the polymeric material is relatively impermeable to the analyte of interest, less analyte reaches the electrodes 520, 522 from the inner tear film layer 40 and the measured amperometric current is therefore systematically lower, and vice versa. The systematic effects on the measured amperometric currents can be accounted for by a scaling factor in relating measured amperometric currents to tear film concentrations. Although after the eye-mountable device is in place over the eye for a period of time, the analyte concentration itself can be influenced by the permeability of the polymeric material 220 if the analyte is one which is supplied to the tear film by the atmosphere, such as molecular oxygen. For example, if the polymeric material 220 is completely impermeable to molecular oxygen, the molecular oxygen concentration of the inner tear film layer 40 can gradually decrease over time while the eye is covered, such as by an exponential decay with a half-life given approximately by the time for half of the oxygen molecules in the inner tear film layer 40 to diffuse into the corneal tissue. On the other hand, where the polymeric material 220 is completely oxygen permeable, the molecular oxygen concentration of the inner tear film layer 40 can be largely unaffected over time, because molecular oxygen that diffuses into the corneal tissue is replaced by molecular oxygen that permeates through the polymeric material 220 from the atmosphere.

FIG. 5B shows an example configuration where an electrochemical sensor detects an analyte from the tear film that contacts the sensor via a channel 530 in the polymeric material 220. The channel 530 has side walls 532 that connect the concave surface 226 of the polymeric material 220 to the substrate 230 and/or electrodes 520, 522. The channel 530 can be formed by pressure molding or casting the polymeric material 220 for example. The height of the channel 530 (e.g., the length of the sidewalls 532) corresponds to the separation between the inward-facing surface of the substrate 230 and the concave surface 226. That is, where the substrate 230 is positioned about 10 micrometers from the concave surface 226, the channel 530 is approximately 10 micrometers in height. The channel 530 fluidly connects the inner tear film layer 40 to the sensor electrodes 520, 522. Thus, the working electrode 520 is in direct contact with the inner tear film layer 40. As a result, analyte transmission to the working electrode 520 is unaffected by the permeability of the polymeric material 220 to the analyte of interest. The indentation 542 in the concave surface 226 also creates a localized increased volume of the tear film 40 near the sensor electrodes 520, 522. The volume of analyte tear film that contributes analytes to the electrochemical reaction at the working electrode 520 (e.g., by diffusion) is thereby increased. The sensor shown in FIG. 5B is therefore less susceptible to a diffusion-limited electrochemical reaction, because a relatively greater local volume of tear film surrounds the sampled region to contribute analytes to the electrochemical reaction.

FIG. 5C shows an example configuration where an electrochemical sensor detects an analyte from the tear film 40 that diffuses through a thinned region 542 of the polymeric material 220. The thinned region 542 can be formed as an indentation 540 in the concave surface 226 (e.g., by molding, casting, etc.). The thinned region 542 of the polymeric material 220 substantially encapsulates the electrodes 520, 522, so as to maintain a biocompatible coating between the cornea 20 and the working electrodes 520, 522. The indentation 542 in the concave surface 226 also creates a localized increased volume of the tear film 40 near the sensor electrodes 520, 522. A directional arrow 544 illustrates the diffusion of the analyte from the inner tear film layer 40 to the working electrode 520.

Figure 5F:
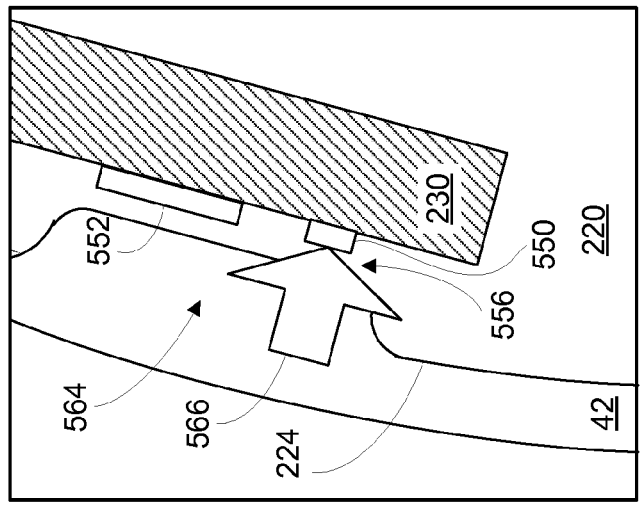
FIG. 5F shows another example configuration in which an electrochemical sensor detects an analyte that diffuses from a tear film layer through a thinned region of a polymeric material, in accordance with one embodiment.
Figure 5E:
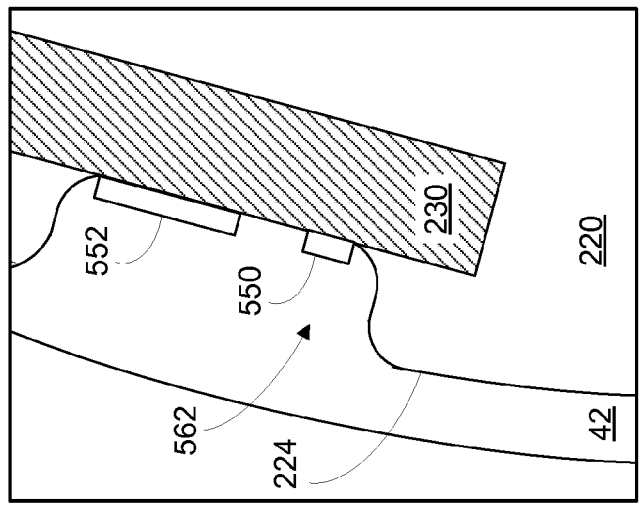
FIG. 5E shows another example configuration in which an electrochemical sensor detects an analyte a tear film layer that contacts the sensor via a channel in a polymeric material, in accordance with one embodiment.
Figure 5D:
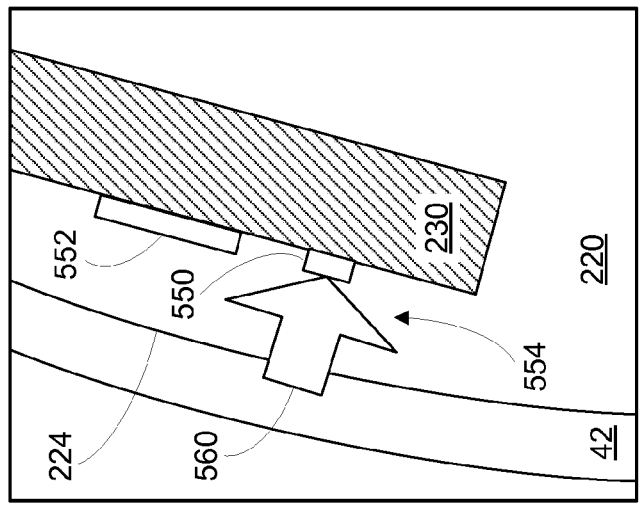
FIG. 5D shows another example configuration in which an electrochemical sensor detects an analyte that diffuses from a tear film layer through a polymeric material, in accordance with one embodiment.

FIG. 5D shows an example configuration in which an electrochemical sensor detects an analyte that diffuses from an outer tear film 42 layer through a polymeric material 220. The working electrode 520 and the reference electrode 522 are each mounted on an outward-facing side of the substrate 230 (e.g., the outward-facing surface 234 discussed in connection with FIG. 2 above). The electrodes 520, 522 of the electrochemical sensor are entirely covered by an overlapping portion 554 of the polymeric material 220. The electrodes 520, 522 in the electrochemical sensor are thus separated from the outer tear film layer 42 by the thickness of the overlapping portion 554. The thickness of the overlapping region 554 can be approximately 10 micrometers, for example. An analyte in the outer tear film layer 42 diffuses through the overlapping portion 554 to the working electrode 520. The diffusion of the analyte from the outer tear film layer 42 to the working electrode 520 is illustrated by the directional arrow 560.

FIG. 5E shows an example configuration in which an electrochemical sensor detects an analyte in an outer tear film layer 42 that contacts the sensor via a channel 562 in a polymeric material 220. The channel 562 connects the convex surface 224 of the polymeric material 220 to the substrate 230 and/or electrodes 520, 522. The channel 562 can be formed by pressure molding or casting the polymeric material 220 for example. The height of the channel 562 corresponds to the separation between the outward-facing surface of the substrate 230 (e.g., the outward-facing surface 234 discussed in connection with FIG. 2 above) and the convex surface 224. That is, where the substrate 230 is positioned about 10 micrometers from the convex 224, the channel 562 is approximately 10 micrometers in height. The channel 562 fluidly connects the outer tear film layer 42 to the sensor electrodes 520, 522. Thus, the working electrode 520 is in direct contact with the outer tear film layer 42. As a result, analyte transmission to the working electrode 520 is unaffected by the permeability of the polymeric material 220 to the analyte of interest. The channel 562 in the convex surface 224 also creates a localized increased volume of the tear film 42 near the sensor electrodes 520, 522. The volume of analyte tear film that contributes analytes to the electrochemical reaction at the working electrode 520 (e.g., by diffusion) is thereby increased. The sensor shown in FIG. 5E is therefore less susceptible to a diffusion-limited electrochemical reaction, because a relatively greater local volume of tear film surrounds the sampled region to contribute analytes to the electrochemical reaction.

FIG. 5F shows an example configuration in which an electrochemical sensor detects an analyte that diffuses from an outer tear film layer 42 through a thinned region of a polymeric material 220. The thinned region 556 can be formed as an indentation 564 in the convex surface 224 (e.g., by molding, casting, etc.). The thinned region 556 of the polymeric material 220 substantially encapsulates the electrodes 520, 522. The indentation 564 in the convex surface 224 also creates a localized increased volume of the tear film 42 near the sensor electrodes 520, 522. A directional arrow 566 illustrates the diffusion of the analyte from the outer tear film layer 42 to the working electrode 520.

FIGS. 5A through 5C illustrate arrangements in which an electrochemical sensor is mounted on a surface of the substrate 230 proximate the concave surface 226 (e.g., the inward-facing surface 232 discussed in connection with FIG. 2 above). An electrochemical sensor arranged as shown in FIGS. 5A through 5C is thus configured to detect an analyte concentration of the inner tear film layer 40, which diffuses into the polymeric material 220 from the concave surface 226. FIGS. 5D through 5F illustrate arrangements in which an electrochemical sensor is mounted on a surface of the substrate 230 proximate the convex surface 224 (e.g., the outward-facing surface 234 discussed in connection with FIG. 2 above). An electrochemical sensor arranged as shown in FIGS. 5D through 5F is thus configured to detect an analyte concentration of the outer tear film layer 42, which diffuses into the polymeric material 220 from the convex surface 224. By situating the electrochemical sensor on the outward-facing surface of the substrate 230, as shown in FIGS. 5D through 5F, for example, the electrodes 520, 522 are separated from the cornea 20 of the eye 10 by the substrate 230. The substrate 230 can thus shield the cornea 20 from damage associated with direct exposure to the electrodes 520, 522, such as may occur due to puncturing or wearing through the polymeric material 220, for example.

V. Example Sensor Pre-Treatment and Calibration

Figure 6A:
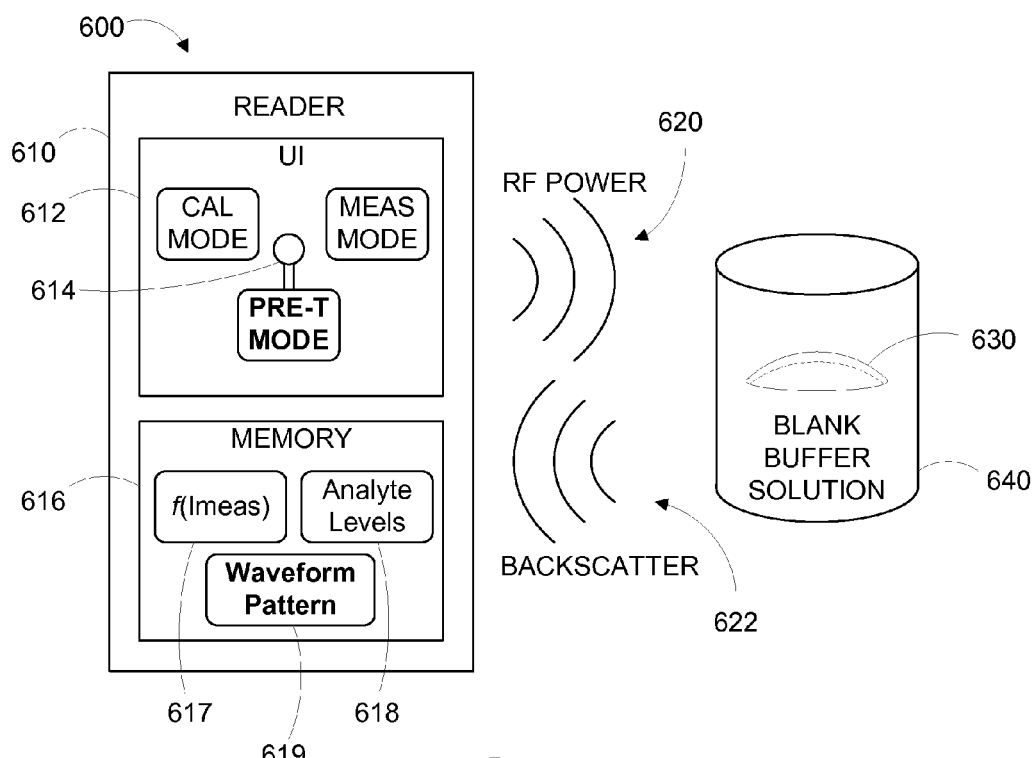
FIG. 6A illustrates an example scenario in which a reader and an eye-mountable device are being used in a pre-treatment mode, in accordance with one embodiment.
Figure 6B:
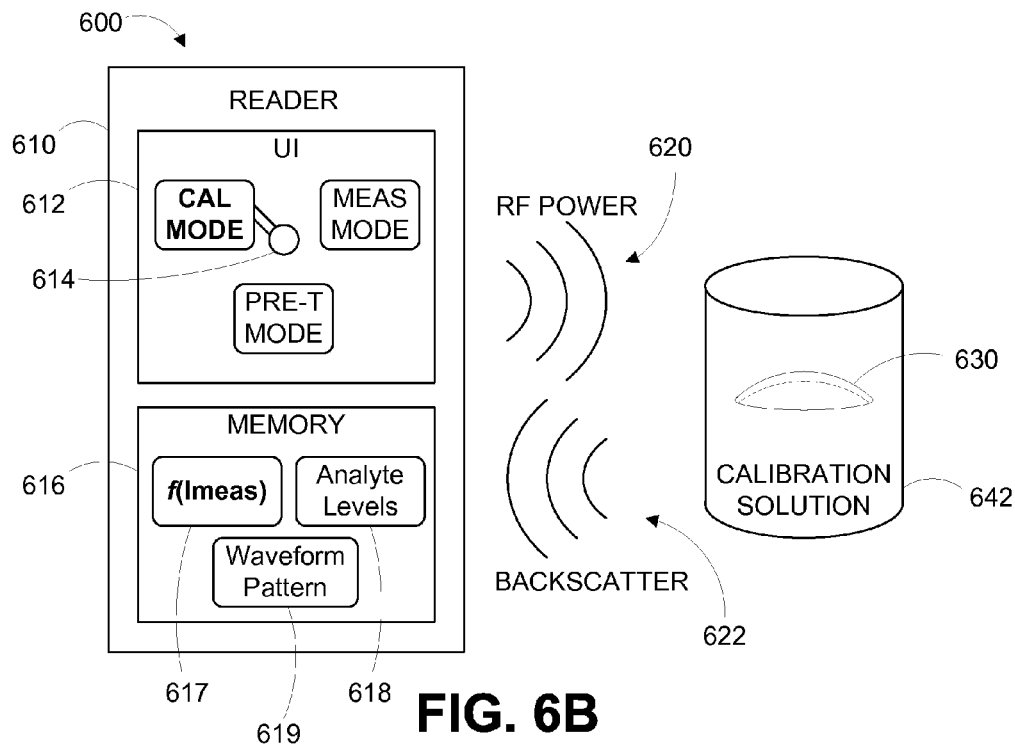
FIG. 6B illustrates an example scenario in which a reader and an eye-mountable device are being used in a calibration mode, in accordance with one embodiment.
Figure 6C:
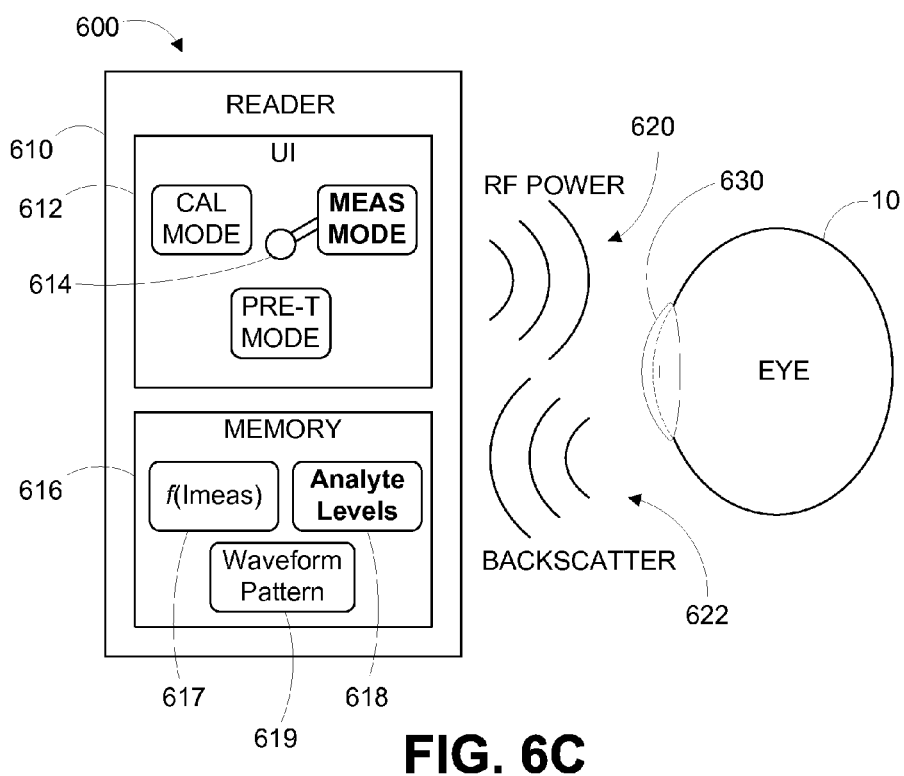
FIG. 6C illustrates an example scenario in which the reader and eye-mountable device of FIG. 6A are being used in a measurement mode, in accordance with one embodiment.

FIG. 6A shows a system 600 with a reader 610 and an eye-mountable device 630 being used in a pre-treatment mode. FIG. 6B is a functional block diagram of the system 600 with the reader 610 and the eye-mountable device 630 being used in a calibration mode. And FIG. 6C is a functional block diagram of the system 600 with the reader 610 and the eye-mountable device 630 being used in a measurement mode. The eye-mountable device 630 can be similar to the eye-mountable devices 110, 210, 310 discussed above in connection with FIGS. 1-3 above and includes an electrochemical sensor embedded within a polymeric material configured to be contact-mounted to an eye. The electrochemical sensor includes a working electrode and a reference electrode and can be operated to generate an amperometric current indicating the concentration of an analyte of interest (e.g., glucose). A reagent layer is localized near the working electrode to sensitize the electrochemical sensor to the analyte of interest. The eye-mountable device 630 is powered to measure an analyte concentration by harvesting energy from incident radio frequency radiation 620. The eye-mountable device 630 wirelessly communicates the sensor results to an external reader 610 by backscatter radiation 622.

The reader 610 includes a user interface 612 to enable selection between the pre-treatment mode, the calibration mode, and the measurement mode. The user interface 610 can include a user input device 614 to receive inputs indicating selection of the pre-treatment mode, the calibration mode, or measurement mode. The user input device 614 is illustrated symbolically as a toggle switch, but can be implemented as any device suitable for receiving user-indicated inputs, such as a touchscreen, a dial, a button, etc. The user input device 614 can be, for example, integrated in a body ("case") of the reader 610. For example, where the reader 610 is implemented as a mobile phone, watch, or other suitably configured portable electronic device, the user input device 614 can be a touchscreen, button, etc. on such device. The user interface 612 can also be implemented via network communication. For example, the case of the external reader may not include any user input device, but can be in network communication with another device that includes user input device. Thus, the user interface 612 can optionally be implemented on a client terminal configured to communicate with the reader 610 and thereby enable selection between the calibration mode and the measurement mode.

The reader 610 also includes a memory 616 storing calibration data 617, sensor results data 618, and pre-treatment data 619. The memory 616 can be a volatile and/or non-volatile computer readable media located in the reader 610 and/or in network communication with the reader 610. The memory 616 can be similar to, for example, the memory 182 in the external reader 180 discussed in connection with FIG. 1 above. The calibration data 617 is used to map sensor readings to analyte concentration levels. The calibration data 617 can include, for example, a function relating sensor readings to analyte concentration levels (e.g., slope and intercept values of a linear relationship), a look-up table relating sensor readings to analyte concentration levels, etc. The sensor results data 618 can include one or more previous tear film analyte concentration levels measured with the system 600. Additionally or alternatively, the sensor results data 618 can also include raw sensor outputs (e.g., amperometric current values). The pre-treatment data 619 can include data for instructing the eye-mountable device to apply an electrical potential waveform pattern between the working electrode and reference electrode. The pre-treatment data 619 can also include data for instructing the eye-mountable device to stop the application of the waveform pattern.

In FIGS. 6A, 6B, and 6C, the pre-treatment mode, calibration mode, and the measurement mode are indicated by the use of bold type on the user interface 612 and the memory 616. In the pre-treatment mode (FIG. 6B) the "PRE-T MODE" text is in bold to indicate that the user input device 614 was used to select the pretreatment mode. In addition, the "Waveform Pattern" text representing the pre-treatment data 619 is in bold to indicate that the pre-treatment data 619 is accessed during the pre-treatment mode. In the calibration mode (FIG. 6B) the "CAL MODE" text is in bold to indicate that the user input device 614 was used to select the calibration mode. In addition, the "f(Imeas)" text representing the calibration data 617 is in bold to indicate that the calibration data 617 is written during the calibration mode. In the measurement mode (FIG. 6C) the "MEAS MODE" text is in bold to indicate that the user input device 614 was used to select the measurement mode. In addition, the "Analyte Levels" text representing the sensor results data 618 is in bold to indicate that the sensor results data 618 is written during the measurement mode.

In the pre-treatment mode (FIG. 6A), the system 600 accesses the pre-treatment data 619 stored in the memory 616 in accordance with the pre-treatment process. The eye-mountable device 630 is exposed to a blank buffer solution, such as a blank PBS solution, which is substantially devoid of the analyte of interest. The eye-mountable device 630 can be exposed to the blank buffer solution 640 in a manner that allows the embedded electrochemical analyte sensor to come in contact with the solution 640. For example, the eye-mountable analyte sensor 630 can be submerged in a vessel filled with the blank buffer solution 640. Selection of the pre-treatment mode with the user input device 614 can generate a pre-treatment-mode input signal that is received by the reader 610 to set the system 600 in the calibration mode.

Selection of the pre-treatment mode with the user input device 614 can prompt the reader 610 to cause the eye-mountable device 630 to apply an electrical potential waveform pattern between the working electrode and reference electrode of the eye-mountable device 630 and obtain at the reader a responsive reading from the eye-mountable device 630. In one embodiment, the reader 610 radiates RF radiation 620 in the particular pattern desired to be applied between the working electrode and reference electrode. This pattern may be stored in pre-treatment data 619. In an alternative embodiment, the reader 610 transmits via RF radiation 620 an instruction to begin a pre-programmed application of electrical potential waveform patterns. Responsively, the eye-mountable device, and more particularly, logic 324 in conjunction with a specially programmed potentiostat, applies a waveform pattern.

As mentioned, this application of electrical potential to the sensor in the presence of the blank buffer solution may cause microscopic gas bubbles to form in the buffer solution that effectively clean the surface of the sensor's electrode.

Figure 7:
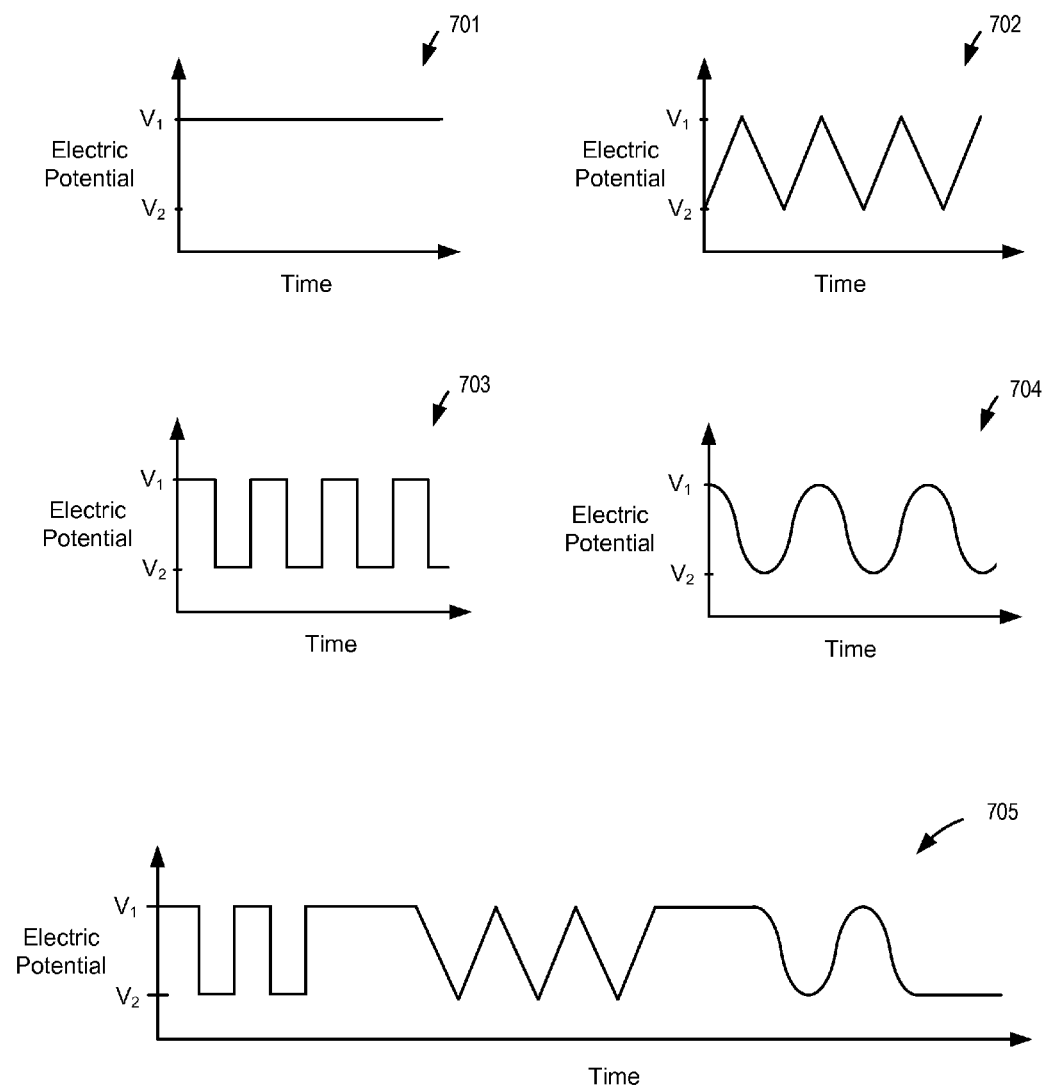
FIG. 7 depicts graphs illustrating example electrical potential waveform patterns, in accordance with one embodiment, in accordance with one embodiment.

FIG. 7 depicts five graphs illustrating example electric potential waveform patterns that may be applied at the eye-mountable device during the pre-treatment mode. The voltage levels $V_1$ and $V_2$, as depicted in the graphs of FIG. 7, may be at or near the voltage levels applied between the working electrode and the reference electrode of eye-mountable device 630 during the measurement mode. For example, in one embodiment $V_1$ is about 1.0 Volt, whereas $V_2$ is about 0.5 Volts. However, other voltage values are possible in other embodiments.

Graph 501 depicts a constant waveform pattern, in which the applied potential remains substantially constant at voltage level $V_1$. Graph 502 depicts a triangle potential waveform pattern, in which the applied potential linearly increases from voltage level $V_2$ to voltage level $V_1$, followed by a linear decrease from voltage level $V_1$ to voltage level $V_2$. Graph 503 depicts a pulse-step waveform pattern, in which the applied potential alternates back and forth between voltage level $V_1$ and voltage level $V_2$. And graph 504 depicts a sine wave waveform pattern, in which the applied potential oscillates between voltage level $V_1$ and voltage level $V_2$ according to a sine function. In some embodiments, the electrical waveform pattern applied during the pre-treatment mode is a combination of one or more of the above-described waveform patterns. For instance, graph 505 depicts an example combination of the above-described waveform patterns, in which a pulse-step waveform is applied, followed by a constant potential, followed by a triangle waveform, followed by a constant potential, followed by a sine wave waveform, followed by a constant potential. Graphs 501-505 depict example waveform patterns, applied in accordance with example embodiments. In other embodiments, other waveform patterns and other combinations of waveform patterns are possible.

During the pre-treatment mode, the reader 610 interrogates the eye-mountable device 630 at various times to obtain a reading in a manner similar to the process 420 discussed in connection with FIG. 4B above. For example, the reader 610 can radiate radio frequency radiation 620 to power the eye-mountable device 630, and receive backscatter radiation 622 indicating the measurement result of the electrochemical sensor embedded in the eye-mountable device 630. In one example, this measurement result represents the amount of current at the working electrode. In response to receiving each measurement, the reader 610 determines whether the measurement is less than a threshold level. When the reader 610 determines that the measurement is less than a threshold level, the reader 610 causes the eye-mountable device 630 to stop the application of the electrical potential waveform pattern.

Figure 8:
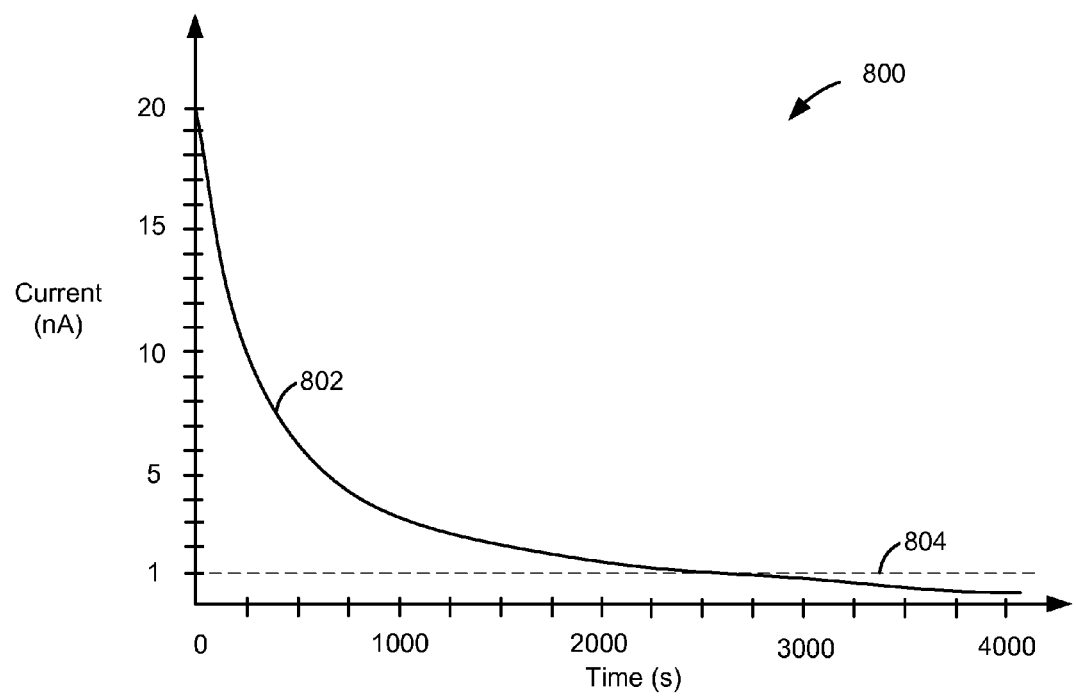
FIG. 8 depicts a graph illustrating an example current level during a pre-treatment mode, in accordance with one embodiment, in accordance with one embodiment.

FIG. 8 is an example graph 800 depicting the current 802 at the working electrode during an example pre-treatment mode. As depicted, at the outset of the application of an electrical potential waveform pattern in the pre-treatment mode, the current 802 at the working electrode is about 20 nA. As further depicted, over the span of about 2500 seconds, this current 802 drops to an example threshold level 804 of about 1 nA. In accordance with one embodiment, in response to determining that the current 802 has dropped to the threshold level 804, the reader 610 causes the eye-mountable device 630 to stop applying the electrical potential waveform pattern. In the embodiment depicted in FIG. 8, the example threshold current level 804 is about 1.0 nA. However, in other embodiments, the threshold level is a percentage (e.g., 1.0%) of the current that flows at the working electrode during the measurement mode (that is, while the eye-mountable device is exposed to the analyte of interest, in for example, tear film). In other embodiments, other currents and other threshold values are possible.

In another embodiment, as an alternative to the reader 610 determining that the current level 802 has dropped to a particular threshold level, the reader 610 determines that the current has remained within a threshold range for a threshold period of time. In one example application of this, if the reader 610 determines that the current has dropped less than 20% in a span of 60 seconds, the reader 610 may responsively cause the eye-mountable device 630 to stop applying the electrical potential waveform pattern. In this embodiment, the most recent current level at the time the reader 610 causes the eye-mountable device 630 to stop applying the electrical potential waveform pattern may be used by the reader 610 as a calibration level, in accordance with the procedure set forth below. The values mentioned with respect to the embodiments discussed above are merely examples, and in other embodiments, other threshold ranges and threshold periods of time are possible.

Figure 9:
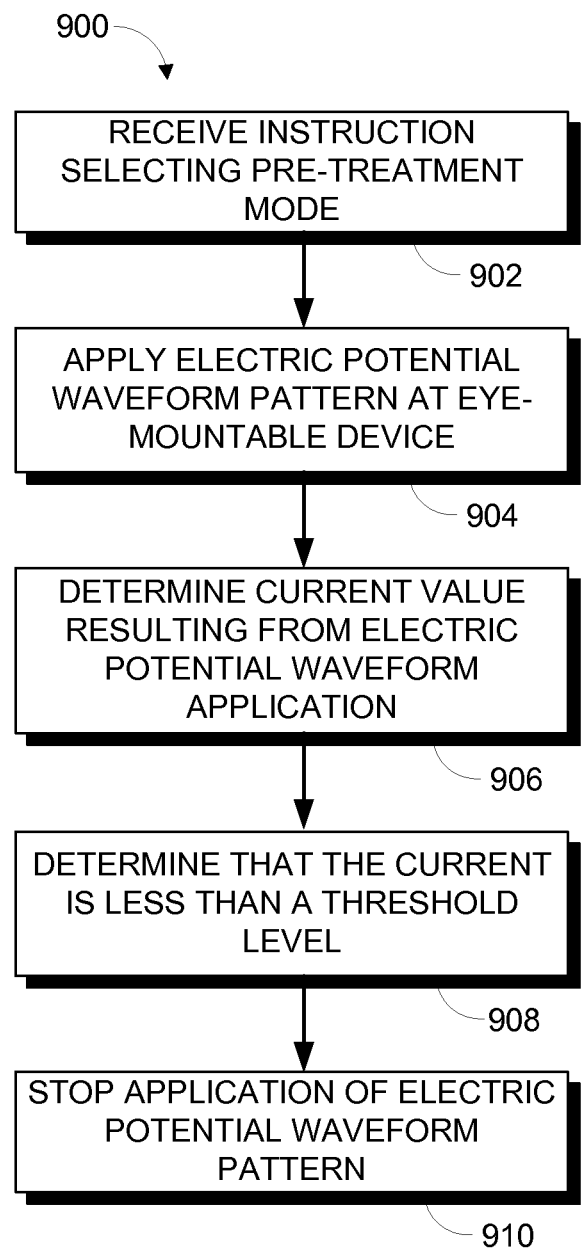
FIG. 9 is a flowchart of an example pre-treatment process, in accordance with one embodiment, in accordance with one embodiment.

FIG. 9 is a flowchart of an example process 900 for engaging in a pre-treatment process. The example process 900 may include one or more operations, functions, or actions, as depicted by one or more of blocks 902, 904, 906, 908, and/or 910, each of which may be carried out by any of the systems described by way of FIGS. 1-6; however, other configurations could be used.

Furthermore, those skilled in the art will understand that flow diagrams described herein illustrate functionality and operation of certain implementations of example embodiments. In this regard, each block of each flow diagram may represent a module, a segment, or a portion of program code, which includes one or more instructions executable by a processor (e.g., processor 186 described above with respect to reader 180) for implementing specific logical functions or steps in the process. The program code may be stored on any type of computer readable medium (e.g., computer readable storage medium or non-transitory media, such as data storage 183 described above with respect to reader 180), for example, such as a storage device including a disk or hard drive. In addition, each block may represent circuitry that is wired to perform the specific logical functions in the process. Alternative implementations are included within the scope of the example embodiments of the present application in which functions may be executed out of order from that shown or discussed, including substantially concurrent or in reverse order, depending on the functionality involved, as would be understood by those reasonably skilled in the art.

The process 900 begins at block 902 where an instruction indicating selection of the pre-treatment mode is received. For example, a pre-treatment mode signal may be received from the user input device 614. Flow continues at block 904, where, in response to receiving the instruction of block 902, an electric potential waveform pattern is applied between the working electrode and reference electrode of eye-mountable device. For example, a combination of one or more of the waveform patterns depicted in FIG. 7 (as well as other not depicted) may be applied at eye-mountable device 630.

Continuing at block 906, the current value at the working electrode resulting from the application of the waveform pattern is determined. For example, the reader 610 may interrogate the eye-mountable device 630 and responsively receive from the eye-mountable device 630 an indication of the current at the eye-mountable device's working electrode.

At block 908, it is determined that the current level is less than a threshold current level. As described above, the reader 630 may determine that the current at the working electrode is less than a threshold level (e.g., about 1.0 nA, or about 1.0% of the current expected at the working electrode during the measurement mode). Alternatively, the reader may determine that the current has remained within a threshold range for a threshold period of time (e.g., within 20% for 60 seconds).

And at block 910, in response to the determination that the current is less than a threshold level in block 908, the application of electric potential at the eye-mountable device is stopped. For example, the reader 610 may transmit an instruction to the eye-mountable device to stop applying the electric potential.

Referring back to FIG. 6B, in the calibration mode, the system 600 updates the calibration data 617 stored in the memory 616 in accordance with a calibration-solution sensor reading. The eye-mountable device 630 is exposed to a calibration solution 642 with a known analyte concentration. In one embodiment, the calibration solution is the blank buffer solution 640 (FIG. 6A) with a known analyte concentration added thereto; alternatively, the calibration solution 642 is a new solution. In any case, the eye-mountable device 630 can be exposed to the calibration solution 642 in a manner that allows the embedded electrochemical analyte sensor to sense the analyte concentration of the calibration solution 642. For example, the eye-mountable analyte sensor 630 can be submerged in a vessel filled with the calibration solution 642, a drop of calibration solution can be placed on the eye-mounting surface (e.g., concave surface) of the eye-mountable device 630, etc. Selection of the calibration mode with the user input device 614 can generates a calibration-mode input signal that is received by the reader 610 to set the system 600 in the calibration mode.

Selection of the calibration mode with the user input device 614 can prompt the reader 610 to obtain a reading from the eye-mountable device 630. The reader 610 interrogates the eye-mountable device 630 to obtain a reading in a manner similar to the process 420 discussed in connection with FIG. 4B above. For example, the reader 610 can radiate radio frequency radiation 620 to power the eye-mountable device 630, and receive backscatter radiation 622 indicating the measurement result of the electrochemical sensor embedded in the eye-mountable device 630.

The calibration-solution sensor result is used to update (and/or create) the calibration data 617 in the memory 616. The calibration data 617 can be updated by determining a functional relationship for mapping sensor readings to analyte concentrations. Such a functional relationship can be based entirely on the calibration-solution sensor result. The newly determined functional relationship can additionally or alternatively be based on the calibration-solution sensor result in combination with previously measured calibration data points and/or other assumptions or predictions, etc. Example calibration procedures for determining a new linear functional relationship mapping sensor readings to analyte concentrations from a single calibration-solution sensor result are described in connection with FIG. 8 below. However, it is noted that the present disclosure applies to calibrations of relationships other than linear relationships, such as higher-order polynomial functional relationships, a look-up table, etc.

Referring to FIG. 6C, in the measurement mode, the system 600 is operated to obtain measurements of tear film analyte concentrations. The eye-mountable device 630 is shown mounted on eye 10, where it can be exposed to a tear film. The user input device 614 is toggled to the measurement mode. Setting the user input device 614 to measurement mode can generate a measurement-mode input signal received via the user interface 612 to instruct the reader 610 that the system 600 is in measurement mode, and the eye-mountable device 630 is ready to obtain measurements of tear film analyte concentrations. The reader 610 obtains a sensor reading from the eye-mountable device 630. The reader 610 can interrogate the eye-mountable device 630 to obtain a reading in a manner similar to the process 420 discussed in connection with FIG. 4B above. For example, the reader 610 can radiate radio frequency radiation 620 to power the eye-mountable device 630, and then receive backscatter radiation 622 indicating the measurement result of the electrochemical sensor embedded in the eye-mountable device 630. While in the measurement mode, the sensor results data 618 in the memory 616 is updated with the sensor readings obtained from the eye-mountable device 630.

By including the user interface 612, the reader 610 can be instructed as to whether the eye-mountable device 630 is situated to engage in the pre-treatment process (e.g., while exposed to the blank buffer solution), obtain a calibration-solution reading (e.g., while exposed to the calibration solution 640), or to obtain a tear-film reading (e.g., while mounted to the eye 10 for exposure to tear film).

Figure 6D:
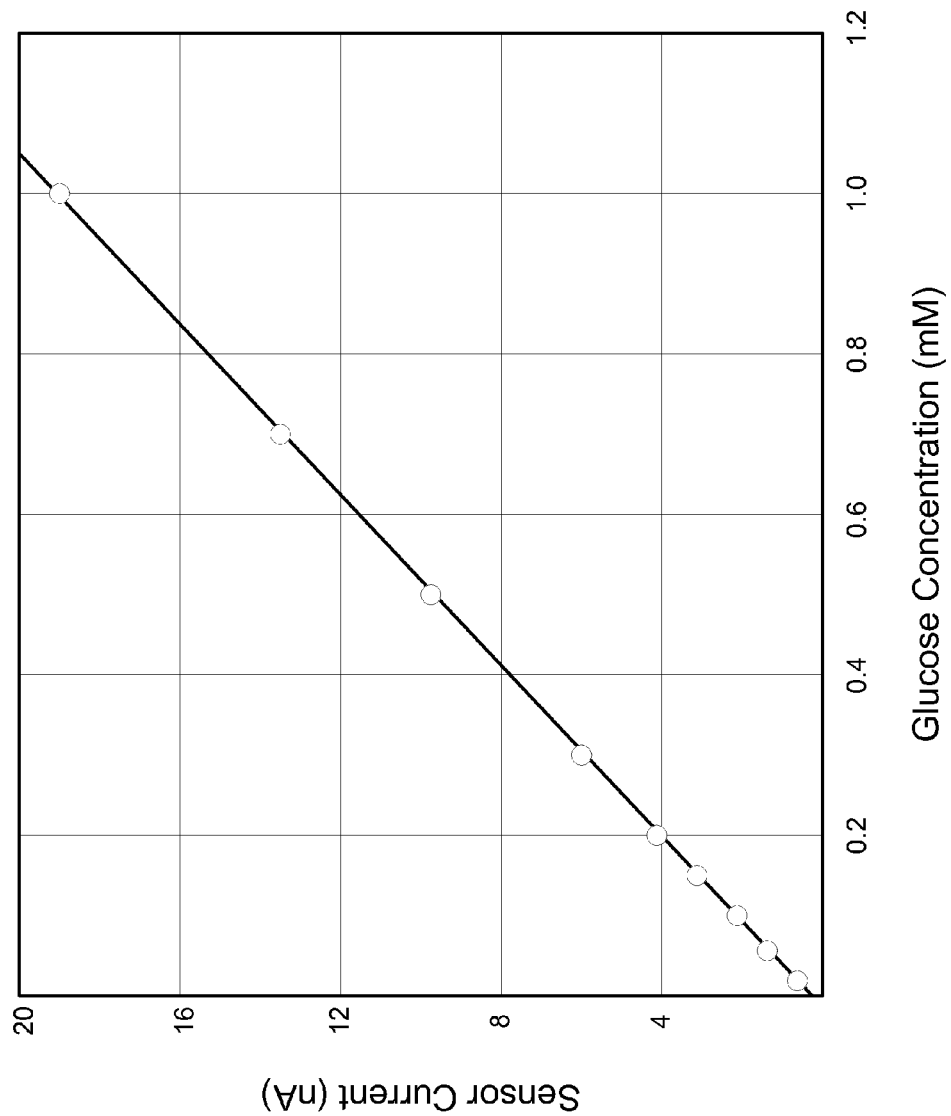
FIG. 6D is a graph showing example amperometric current values for a range of glucose concentrations, in accordance with one embodiment.

FIG. 6D is a graph showing example amperometric current values for a range of glucose concentrations. The amperometric current values correspond to measurements by an electrochemical sensor configured to sense glucose. The electrochemical sensor includes a working electrode and a reference electrode driven by a potentiostat. The potentiostat can apply a voltage between the electrodes sufficient to induce electrochemical reactions at the working electrode and thereby generate an amperometric current while measuring the amperometric current. Glucose oxidase is localized near the working electrode to sensitize the sensor to glucose. The glucose oxidase catalyzes glucose to create hydrogen peroxide, which is then oxidized at the working electrode to generate the amperometric current. Human tear film glucose concentrations can range from about 0 millimolar to about 1 millimolar (mM). To calibrate the electrochemical glucose sensor current response over the clinically relevant range, calibration solutions with known glucose concentrations can be prepared between about 0 mM and about 1 mM, and sensor readings can be obtained while the sensor is exposed to each of the calibration solutions, similar to the calibration mode operation of the system 600 described above in connection with FIG. 6A. For example, the external reader 610 can obtain sensor readings by interrogating the eye-mountable device 630 to perform a measurement while the eye-mountable device 630 is exposed to a calibrated solution. The external reader 610 can then wirelessly receive the sensor result similar to the process. Example results from such a procedure are shown as circles in the graph in FIG. 6D and are listed in the table below.

| Glucose Concentration [mM] | Measured Current [nA] |
| --- | --- |
| 0.02 | 0.60 |
| 0.06 | 1.36 |
| 0.10 | 2.13 |
| 0.15 | 3.12 |
| 0.20 | 4.04 |
| 0.30 | 6.01 |
| 0.50 | 9.74 |
| 0.70 | 13.4 |
| 1.00 | 19.0 |

The calibration data shows a substantially linear relationship between glucose concentration and measured current. The trend line included in the graph in FIG. 6D defines a relationship relating sensor current and glucose concentration over the clinically relevant range of about 0 mM to about 1 mM. The trend line relates the measured currents to the calibrated glucose concentrations. The trend line can be used to determine analyte concentration as a function of sensor current, which can then be used to relate future amperometric current measurements to analyte concentrations. For example, in measurement mode of the system 600 described in connection with FIG. 6B, the external reader 610 can be programmed to map amperometric currents to corresponding analyte concentrations according to a functional relationship dependent on the amperometric current. That is, a functional relationship can be determined from the calibration data of the form:

$$AC = f(Imeas),$$

where AC is the analyte concentration, Imeas is the measured amperometric current, and $f$ represents the functional form stored in the external reader 610 as the calibration data 617. Similarly, the external reader 340 described in connection with FIG. 3 can be configured to map measured amperometric currents to analyte concentrations according to a function determined in part by calibration data.

The functional form of the relationship relating measured amperometric currents and analyte concentrations can be set according to an empirically derived calibration data set, according behavior of similar devices, and/or according to theoretical predictions. For example, an eye-mountable electrochemical analyte sensor can be calibrated in connection with its manufacturing process by obtaining sensor outputs (e.g., amperometric currents) while the sensor is exposed to one or more solutions with known analyte concentrations.

In some embodiments, one or more calibration data points (e.g., a measured sensor result for a known analyte concentration) can be used to determine the functional form of a relationship relating measured current and analyte concentration. For example, any two such calibration data points can be used to solve for coefficients in a first-degree polynomial (e.g., a linear function) by fitting a line to the data points. Additional calibration data points can be used to determine a functional relationship based on a higher order polynomial (e.g., a quadratic functional relationship, etc.). Additionally or alternatively, the functional relationship determined by calibration data can be determined according to a minimization technique (e.g., minimization of $\chi^2$, etc.) where there are a greater number of calibration data points than degrees of freedom in the functional relationship. Moreover, in some embodiments, a look-up table listing sensor readings and corresponding analyte concentration levels can be used to map sensor readings to analyte concentrations. For example, entries in such a look-up table can be interpolated to associate a tear film sensor reading with an analyte concentration. In some embodiments, a calibration can be performed on one or more of a batch of eye-mountable electrochemical sensors manufactured under similar conditions, and the derived calibrated functional relationship can be loaded to each such sensor in the batch.

VI. Example Single-Point Sensor Calibration

In some embodiments, a technique can be used to determine a functional relationship relating the amperometric current and the concentration of analyte using only one calibration data point. For example, a single calibration data point (e.g., sensor result while the sensor is exposed to a solution with a known analyte concentration paired with the known analyte concentration) can be used in combination with assumptions and/or previous calibration data to determine a functional relationship relating sensor results to analyte concentrations.

FIG. 10A is a flowchart of an example process 1000 for calibrating an eye-mountable device with a single calibration data point. A user input indicating selection of the calibration mode is received (1002). For example, a calibration-mode signal can be received from the user input device 614. A calibration-solution sensor reading is received (1004). The calibration-solution sensor reading can be obtained, for example, by the system 600 operated in the calibration mode as shown in FIG. 6A. For example, the eye-mountable device 630 can be exposed to the calibration solution 640, and the reader 610 can interrogate the eye-mountable device 630 to obtain a reading. A calibration value is determined to relate sensor readings to analyte concentrations (1006). The calibration value can be, for example, a functional form mapping sensor results to analyte concentrations. For example, the calibration value can be a slope and/or intercept defining a linear relationship, an entry in a look-up table, etc. The determined calibration value can be stored for use in interpreting future readings from the eye-mountable analyte sensor (e.g., in the calibration data 617). Thus, at the conclusion of block 1004, the eye-mountable device 630 is calibrated and the calibration information is stored in the reader 610 for future use in interpreting sensor readings.

For illustrative purposes only, an example is described in detail where a single calibration-solution sensor result is used, without more, to determine a linear relationship mapping sensor readings to analyte concentrations. The functional form can be determined by solving for a linear relationship that passes through the calibration data point and the origin. Thus, the relationship is assumed to be linear, and a zero current reading is assumed to correspond to an analyte concentration of zero. The determination of the relationship then amounts to solving for the slope of such a linear relationship where the intercept is held fixed (e.g., at zero). The functional form of such a relationship in terms of Imeas is then:

AC=f(Imeas)=(ACcal/Ical)Imeas, where ACcal is the analyte concentration of the calibration solution, Ical is the sensor current measured while the eye-mountable analyte sensor is exposed the calibration solution. The slope of the linear relationship is therefore the sensitivity of the eye-mountable analyte sensor: ACcal/Ical. It is noted that the intercept can be assumed to be another value other than zero while still solving for the slope of a linear relationship. For example, an analyte concentration of zero can still register a low level amperometric current due to, for example, ions, enzymes, etc. that electrochemically react with the sensor even in the absence of the analyte. Moreover, in some embodiments, a linear relationship can be determined by using the calibration data point to solve for an intercept value (e.g., current level for zero analyte concentration) of a linear relationship while keeping the slope (e.g., sensitivity) of the relationship fixed.

A user input indicating selection of the measurement mode is received (1008). For example, a measurement-mode signal can be received from the user input device 614. However, it is noted the process 1000 can be implemented without block 1008 where, for example, the system 600 is configured to automatically default back to the measurement mode upon completion of a calibration operation. In blocks 1010 and 1012 tear-film sensor readings are mapped to tear film analyte concentration levels in accordance with the calibration carried out in blocks 1002-1006. A tear-film sensor reading is received (1010). The tear-film sensor reading can be obtained, for example, by the system 600 operated in the measurement mode as shown in FIG. 6B. For example, the eye-mountable analyte sensor 630 can be exposed to tear film by mounting the eye-mountable device 630 to the eye 10, and the reader 610 can interrogate the eye-mountable device 630 to obtain a reading. A tear film analyte concentration is determined based on the tear-film sensor reading and the calibration value (1012). Thus, the calibration value allows for mapping sensor results to analyte concentration levels. For example, where the calibration information includes a functional relationship relating sensor readings to analyte concentrations, the analyte concentration can be determined according to such a functional relationship.

VII. Example Multi-Point Sensor Calibration

FIG. 10B is a flowchart of an example process 1020 for calibrating an eye-mountable analyte sensor with multiple calibration data points. A user input is received indicating a first calibration mode (1022). The first calibration mode is for obtaining a sensor reading while the eye-mountable analyte sensor is exposed to a first calibration solution with a first analyte concentration. The user input can be indicated by, for example, a first-calibration-mode input signal received via a user input device configured to enable selection between a first calibration mode, a second calibration mode, and a measurement mode. Receipt of the first-calibration-mode user input can prompt the reader 610 to interrogate the eye-mountable device 630 for a first-calibration-solution sensor reading. A first-calibration-solution sensor reading is received (1024). A user input is received to indicate a second calibration mode (1026). The second calibration mode is for obtaining a sensor reading while the eye-mountable analyte sensor is exposed to a second calibration solution with a second analyte concentration. Receipt of a second-calibration-mode user input can prompt the reader 610 to interrogate the eye-mountable device 630 for a second-calibration-solution sensor reading. A second-calibration-solution sensor reading is received (1028). The two calibration modes can provide sensor results from two different calibration solutions with different analyte concentrations. For example, the first calibration solution can have an analyte concentration near a mid-range of clinically relevant concentration levels and the second calibration solution can have an analyte concentration near zero (e.g., a buffer made with distilled water).

Thus, at the conclusion of block 1028, two calibration data points are available from the two separate sensor readings while the eye-mountable analyte sensor is exposed to two separate calibration solutions with different analyte concentrations. The two calibration data points can be combined together to determine a calibration value relating the sensor readings to analyte concentrations (1030). The calibration values can include, for example, coefficients in a second order polynomial (i.e., a slope and intercept values) mapping sensor results (e.g., amperometric currents) to analyte concentration levels.

In blocks 1032 and 1034 tear-film sensor readings are mapped to tear film analyte concentration levels in accordance with the calibration carried out in blocks 1022-1030. A tear-film sensor reading is received (1032) and a corresponding tear film analyte concentration is determined (1034).

The calibration operations discussed in connection with blocks 1002-1006 in FIG. 10A and blocks 1022-1030 in FIG. 10B are shown preceding a single tear-film sensor reading operation (e.g., blocks 1010-1012 in FIG. 10A and blocks 1032-1034 in FIG. 10B), however other methods of operation are also possible. The eye-mountable device 630 could be operated intermittently to obtain tear-film sensor readings without an intervening calibration operation between subsequent tear-film sensor readings. For example, the system 600 can be configured to operate in the measurement mode by default and can obtain tear film analyte concentration measurements periodically and/or upon receipt of a prompting signal, such as a signal from the user interface 612, a network-delivered signal, etc. The system can optionally be configured to enter the calibration mode to receive a calibration-solution sensor reading only upon receiving a calibration-mode user input, at which point the reader 610 obtains a single sensor reading (i.e., the calibration-solution sensor reading) and returns to the measurement mode.

In some embodiments, the calibration operation (e.g., blocks 1002-1006 in FIG. 10A and blocks 1022-1030 in FIG. 10B) can be performed multiple times during the lifetime of the eye-mountable device 630 to compensate for variations in the behavior of the eye-mountable device 630 over time. For example, the sensitivity of the electrochemical sensor, which corresponds to the slope of a linear relationship relating measured current to analyte concentration, can change due to: changes in the electrical properties of one or more of the electrodes in the electrochemical sensor, changes in the amount or activity of the reagent proximal to the working electrode, gradual build-up of protein or other materials on or near the electrodes, changes in the distance between the electrodes and the eye-mounting surface (e.g., due to deformation or spreading of the polymeric material in the region over the electrodes), changes in the diffusion characteristics of the polymeric material (in embodiments in which the analyte reacts with the reagent proximal to the working electrode after diffusing through the polymeric material) and/or other reasons.

Moreover, the calibration value determined during the calibration operation (e.g., at blocks 1002 and 1004) can be employed to interpret sensor readings both prospectively and retrospectively. For example, in addition to using the calibration value to determine analyte concentrations for future sensor readings, the calibration value can be used to determine analyte concentrations from previously obtained sensor readings. In some examples, stored analyte concentrations and/or sensor results (e.g., the sensor result data 618) can be re-evaluated upon completion of a calibration operation. For example, each sensor result can be mapped to an analyte concentration level based on the most temporally proximate calibration value(s) available in the calibration data memory 617.

Figure 11A:
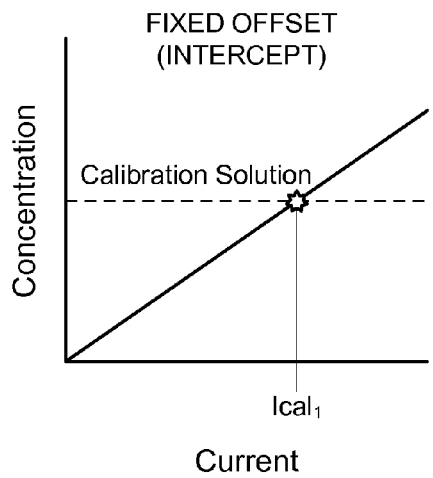
FIG. 11A is an example graph illustrating a single-point calibration technique where the functional form is linear and has a fixed offset, in accordance with one embodiment.
Figure 11B:
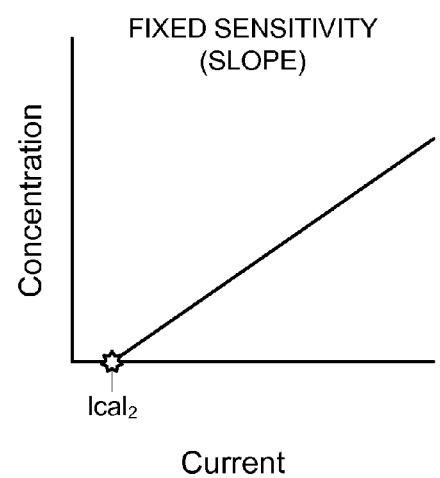
FIG. 11B is a graph illustrating an example single-point calibration technique where the functional form is linear and has a fixed sensitivity, in accordance with one embodiment.
Figure 11C:
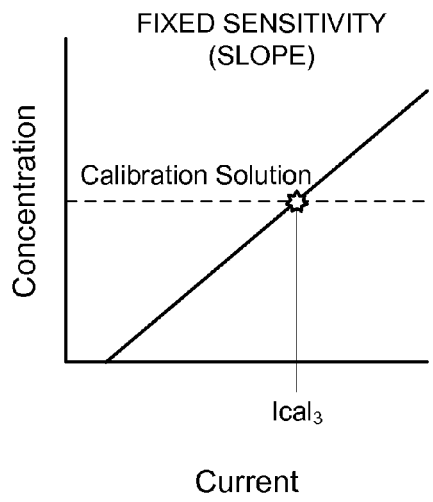
FIG. 11C is a graph illustrating another example single-point calibration technique where the functional form is linear and has a fixed sensitivity, in accordance with one embodiment.
Figure 11D:
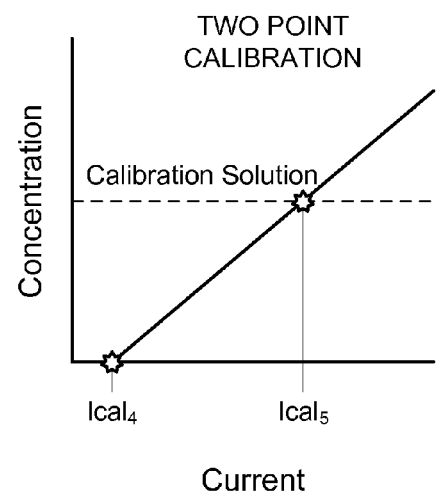
FIG. 11D is a graph illustrating an example two-point calibration technique where the functional form is linear, in accordance with one embodiment.

FIGS. 11A through 11C symbolically illustrate schemes employed herein to use a single calibration data point to determine a relationship to map sensor readings (amperometric current values) to analyte concentration levels. The schemes illustrated in connection with FIGS. 11A-11C can be similar to the process 1000 for single-point calibration described in connection with FIG. 10A. FIG. 11D symbolically illustrates a scheme to use two calibration data points to determine a relationship between sensor readings (current values) and analyte concentration levels. The scheme illustrated in connection with FIG. 11D can be similar to the process 1020 for multi-point calibration described in connection with FIG. 10B.

FIG. 11A is an example graph illustrating a single-point calibration technique where the functional form is linear and has a fixed offset. The single calibration data point is obtained while the eye-mountable device is exposed to a calibration solution with a known analyte concentration. The analyte concentration level of the calibration solution is indicated by the dashed line. The sensor reading results in an amperometric current of $Ical_1$. A linear relationship can then be determined for a line that passes through the origin and the calibration data point (at the concentration level of the calibration solution and the current value $Ical_1$). It is noted however, that in some embodiments the intercept point can be set to a different value other than zero.

FIG. 11B is an example graph illustrating a single-point calibration technique where the functional form is linear and has a fixed sensitivity. In FIG. 11B a single calibration data point is obtained while the eye-mountable device is exposed to a calibration solution with an analyte concentration of zero. The calibration solution used in FIG. 11B can be, for example, a buffer made with distilled water. The sensor reading results in an amperometric current of $Ical_2$. A linear relationship can then be determined for a line with a fixed slope that passes through the calibration data point (at zero analyte concentration level and the current value $Ical_2$). The fixed slope can be based on an assumed sensitivity of the eye-mountable analyte sensor, for example.

FIG. 11C is another example graph illustrating a single-point calibration technique where the functional form is linear and has a fixed sensitivity. In FIG. 11C a single calibration data point is obtained while the eye-mountable device is exposed to a calibration solution with a known analyte concentration. The analyte concentration level of the calibration solution is indicated by the dashed line. The sensor reading results in an amperometric current of $Ical_3$. A linear relationship can then be determined for a line with a fixed slope that passes through the calibration data point (at the concentration level of the calibration solution and the current value $Ical_3$). The fixed slope can be based on an assumed sensitivity of the eye-mountable device, for example.

FIG. 11D is an example graph illustrating a two-point calibration technique where the functional form is linear. A first calibration point is obtained while the eye-mountable device is exposed to a calibration solution with an analyte concentration of zero, which results in an amperometric current of $Ical_4$. The first calibration solution can be, for example, a buffer made with distilled water. A second calibration point is obtained while the eye-mountable device is exposed to a second calibration solution with a known analyte concentration indicated by the dashed line, which results in an amperometric current of $Ical_5$. A linear relationship can then be determined for a line that passes through both calibration data points.

Figure 12:
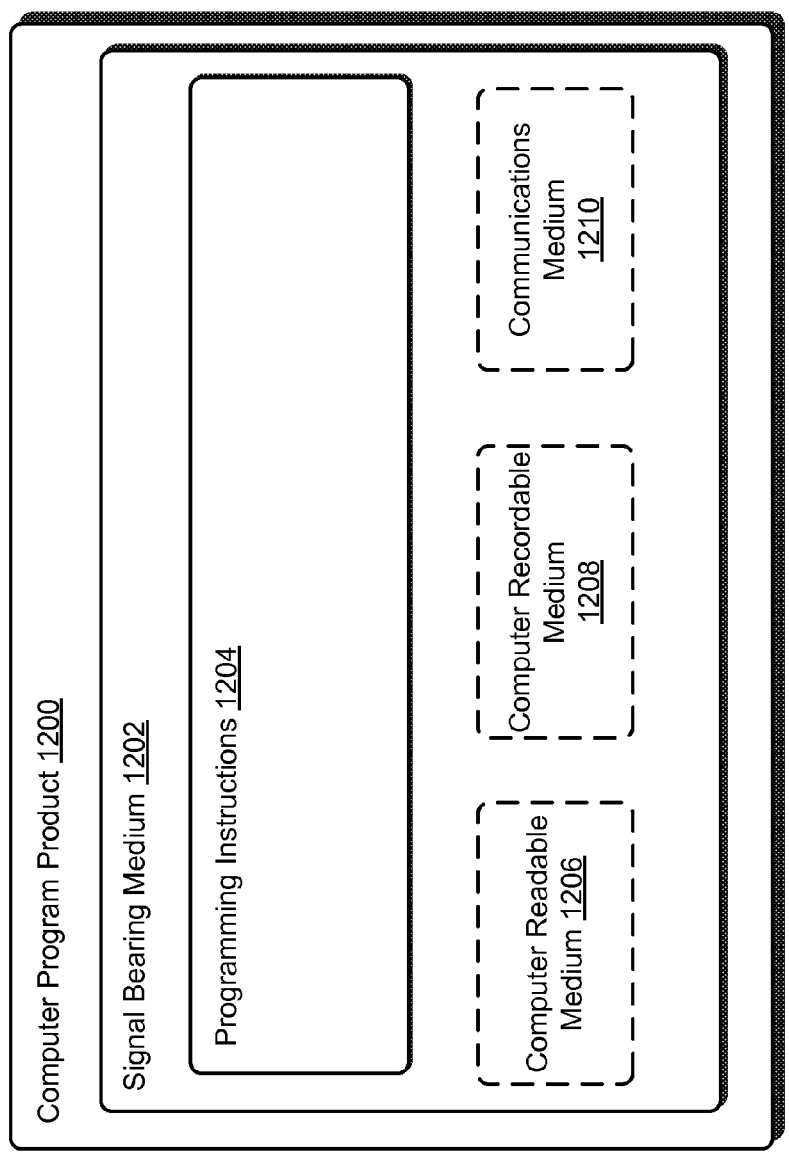
FIG. 12 depicts a computer-readable medium configured, in accordance with one embodiment.

FIG. 12 depicts a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause the system to carry out the various functions, tasks, capabilities, etc., described above.

As noted above, in some embodiments, the disclosed techniques can be implemented by computer program instructions encoded on a non-transitory computer-readable storage media in a machine-readable format, or on other non-transitory media or articles of manufacture (e.g., the instructions 184 stored on the memory storage 182 of the external reader 180 of the system 100). FIG. 12 is a schematic illustrating a conceptual partial view of an example computer program product that includes a computer program for executing a computer process on a computing device, arranged according to at least some embodiments presented herein.

In one embodiment, the example computer program product 1200 is provided using a signal bearing medium 1202. The signal bearing medium 1202 may include one or more programming instructions 1204 that, when executed by one or more processors may provide functionality or portions of the functionality described above with respect to FIGS. 1-8. In some examples, the signal bearing medium 1202 can be a computer-readable medium 1206, such as, but not limited to, a hard disk drive, a Compact Disc (CD), a Digital Video Disk (DVD), a digital tape, memory, etc. In some implementations, the signal bearing medium 1202 can be a computer recordable medium 1208, such as, but not limited to, memory, read/write (R/W) CDs, R/W DVDs, etc. In some implementations, the signal bearing medium 1202 can be a communications medium 1210, such as, but not limited to, a digital and/or an analog communication medium (e.g., a fiber optic cable, a waveguide, a wired communications link, a wireless communication link, etc.). Thus, for example, the signal bearing medium 1202 can be conveyed by a wireless form of the communications medium 1210.

The one or more programming instructions 1204 can be, for example, computer executable and/or logic implemented instructions. In some examples, a computing device such as the processor-equipped external reader 180 of FIG. 1 is configured to provide various operations, functions, or actions in response to the programming instructions 1204 conveyed to the computing device by one or more of the computer readable medium 1206, the computer recordable medium 1208, and/or the communications medium 1210.

The non-transitory computer readable medium 1206 can also be distributed among multiple data storage elements, which could be remotely located from each other. The computing device that executes some or all of the stored instructions could be an external reader, such as the reader 180 illustrated in FIG. 1, or another mobile computing platform, such as a smartphone, tablet device, personal computer, etc. Alternatively, the computing device that executes some or all of the stored instructions could be remotely located computer system, such as a server.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A system comprising:
   a wearable device comprising:
      an antenna;
      an electrochemical sensor that includes a working electrode, a reference electrode, and a reagent that selectively reacts with an analyte; and
      a controller electrically connected to the electrochemical sensor and the antenna, wherein the controller is configured to control the electrochemical sensor to obtain a sensor measurement while the wearable device is exposed to a fluid, and use the antenna to transmit the sensor measurement; and
   a reader operable in a pre-treatment mode and a measurement mode,
      wherein in the pre-treatment mode the reader is configured to (i) wirelessly communicate with the antenna to cause the electrochemical sensor to apply an electric potential waveform pattern between the working electrode and the reference electrode, the pattern comprising a combination of a constant voltage and at least one voltage waveform including one or more of a triangle waveform, a pulse-step waveform, and a sine waveform, (ii) wirelessly communicate with the antenna to receive a pre-treatment measurement obtained while the wearable device is exposed to a buffer solution substantially devoid of the analyte, (iii) determine that the pre-treatment measurement is less than a threshold level, and (iv) in response to the determination, wirelessly communicate with the antenna to cause the wearable device to stop applying the electric potential waveform pattern, and
      wherein in the measurement mode the reader is configured to wirelessly communicate with the antenna to receive a tear-film sensor measurement obtained with the wearable device exposed to a tear film and determine a concentration of the analyte in the tear film based on the tear-film sensor measurement.

2. The system of claim 1, wherein the controller includes a potentiostat that is configured to apply the electric potential waveform pattern between the working electrode and the reference electrode.

3. The system of claim 1, wherein the reader is further configured to supply power to the wearable device through the antenna.

4. The system of claim 1, further comprising a user interface configured to receive a selection of one or more of the pre-treatment mode and the measurement mode.

5. The system of claim 1, wherein the threshold level is a threshold percentage of an operating current resulting from the application of electric potential between the working electrode and the reference electrode while the wearable device is exposed to the analyte.

6. The system of claim 1, wherein the reader is configured to determine that the pre-treatment measurement is less than a threshold level by being configured to determine that the pre-treatment measurement has remained within a threshold range for a threshold period of time.

7. The system of claim 1, wherein the reader is further operable in a calibration mode,
- wherein in the calibration mode, the reader is configured to (i) wirelessly communicate with the antenna to receive a calibration-solution sensor measurement based on the wearable device being exposed to a calibration solution that contains a concentration of the analyte, (ii) determine a calibration value based on at least the calibration-solution sensor measurement and the concentration of the analyte in the calibration solution, and (iii) store the calibration value in a memory, and
- wherein in the measurement mode, the reader is further configured to determine a concentration of the analyte in the tear film based on at least the tear-film sensor measurement and the calibration value.

8. The system of claim 1, wherein the wearable device further comprises a transparent polymeric material having a concave surface and a convex surface, wherein the concave surface is configured to be removably mounted over a corneal surface and the convex surface is configured to be compatible with eyelid motion when the concave surface is so mounted.

* * * * *